(12) United States Patent
Yang et al.

(10) Patent No.: US 7,345,219 B2
(45) Date of Patent: Mar. 18, 2008

(54) MITOGEN-ACTIVATED PROTEIN KINASE AND METHOD OF USE TO ENHANCE BIOTIC AND ABIOTIC STRESS TOLERANCE IN PLANTS

(75) Inventors: Yinong Yang, Fayetteville, AR (US); Lizhong Xiong, Wuhan (CN)

(73) Assignee: The Board of Trustees for the University of Arkansas, Little Rock, AR (US)

( * ) Notice: Subject to any disclaimer, the term of this patent is extended or adjusted under 35 U.S.C. 154(b) by 80 days.

(21) Appl. No.: 10/768,886

(22) Filed: Jan. 31, 2004

(65) Prior Publication Data

US 2004/0209325 A1    Oct. 21, 2004

Related U.S. Application Data

(60) Provisional application No. 60/444,249, filed on Jan. 31, 2003.

(51) Int. Cl.
  *A01H 5/00*    (2006.01)
  *C12N 15/82*   (2006.01)
  *C12N 15/87*   (2006.01)
(52) U.S. Cl. .................. 800/295; 435/468; 800/289
(58) Field of Classification Search ............ None
  See application file for complete search history.

(56) References Cited

OTHER PUBLICATIONS

Zhang et al. (Trends in Plant Science, 6:520-527, 2001).*
Guo et al. (PNAS, 101: 9205-9210, 2004).*
Wen et al. (Plant Physiol., 129:1880-1891, 2002).*
Wen et al. (NCBI, GenBank, Sequence Accession No. AF216314, pp. 1-2, Published Dec. 2000).*
Valvekens et al. (PNAS, 85:5536-5540, 1988).*
Agrawal et al. 2002 Isolation of novel rice multiple stress responsive MAP kniase gene OSMSRMK2 whose mRNA accumulates rapidly in response to environmental cues. BBRC 294:1009.
Asai et al. 2002 MAP inase signalling cascade in Arabidopsis innate immunity. Nature 415:977.
Frye et al. 2001 Negative regulation of defense responses in plants by a conserved MAPK kinase. PNAS 98:373.
Hardin et al. 1998 Molecular cloning and characterization of maize ZmMEK1 a protein kinase with a catalytic domain homologous to mitogen and stress-activated .. Planta 206:577.
Huang et al. 2002 Expression of Oryza sativa MAP kinase gene is developmentally regulated and stress-responsive. Physio. Plant. 114:572.
Jonak et al. 1996 Stress signaling plants: A mitogen-activated protein kinase pathway is activated by cold and drought. PNAS 93:11274.
Kiegeri et al. 2000 SIMKK a Mitogen-Activated Protein Kinase (MAPK) Kinase is a Specific Activator of the Salt Stress-Induced MAPK, SIMK. Plant Cell 12:2247.
Knetsch et al. 1996 Abscisic Acid Induces Mitogen-Activated Protein Kinase Activation in Barley Aleurone Protoplasts. Plant Cell 8:1061.
Mikotjaczk et al. 2000 Osmostic Stress Induces rapid activation of a Salicyclic Acid-Induced Protein Kinase and a Homolog of Protein Kinase ASK1 in Tobacco.. Plant Cell 12:165.
Seo et al. 1999 Jasmonte-based wound signal transduction requires activation of WIPK, a tobacco mitogen-activated protein kinase. Plant Cell 11:289.
Song et al. 2002 OsBIMK1, a rice MAP kinase gene involved in disease resistance responses. Planta 215:997.
Wen et al. 2002 Two novel mitoen-activated protein signaling components, OSMEK1 and OsMAP1 are involved in a moderate low-temperature . . . Plant Physio. 129:1880.
Yang et al. 2001 Activation of a mitogen-activated protein kinase pathway is involved in disease resistance in tobacco. PNAS 98:741.
Zhang et al. 1997 Salicylic Acid Activates a 48-kD MAP Kinas in Tobacco. Plant Cell 9:809.
Zhang et al. 1998 The tobacco wounding-activated mitogen-activated kinase is encoded by SIPK. PNAS 95:7225.
Zhang et al. 1998 Resistance gene N-mediated de novo synthesis and activationof a tobacco mitogen-activated protein kinase by tobacco mosaic virus infection. PNAS 95:7433.
Zhang et al. 2001 MAPK cascades in plant defense signaling. Trends in Plant Science. 6:(11)520.
Zhang et al. 2001 Activation of Salicylic Acid-Induced Protein Kinase, a Mitogen-Activated Protein Kinase, Induces Multiple Defense Responses in Tobacco. Plant Cell 13:1877.

* cited by examiner

*Primary Examiner*—Phuong T. Bui
*Assistant Examiner*—Vinod Kumar
(74) *Attorney, Agent, or Firm*—Angela Foster, Esq.

(57) ABSTRACT

The present invention relates to the mitogen-activated protein kinase called MAPK5. The rice MAPK5 gene, its protein and kinase activity were induced by abscisic acid, pathogen infection, wounding, drought, salt and cold temperature. However, suppression of MAPK5 expression and kinase activity in dsRNAi transgenic plants resulted in constitutive expression of pathogenesis-related genes such as PR-1 and PR-10 but enhanced resistance to fungal and bacterial pathogens. In contrast, overexpressed transgenic lines exhibited elevated MAPK5 kinase activity and increased tolerance to drought, salt and cold stresses. This invention provides methods for increasing tolerance to abiotic and biotic stress in plant using MAPK5.

4 Claims, 14 Drawing Sheets

A

Figure 2:
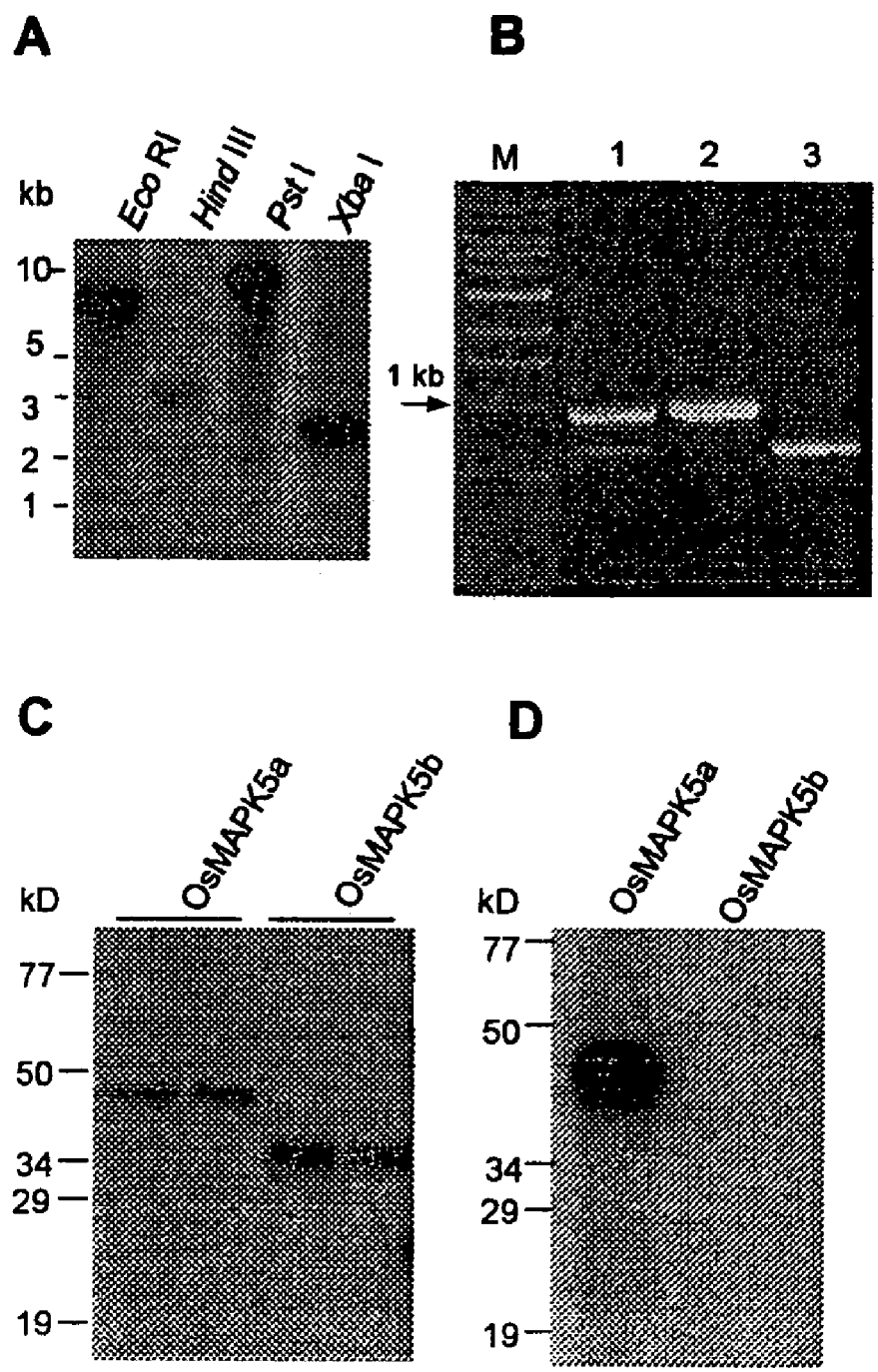

```
OsMAPK5a    -------MDGAPVAEFRPTMTHGGRYLLYDIFGNKFEVTN
OsMAPK5b    -------MDGAPVAEFRPTMTHGGRYLLYDIFGNKFEVTN
TaWCK-1     -------MDGAPVAEFRPTMTHGGRFLLYNIFGNQFEITA
NtWIPK      MADANMGAGGGQFPDFPSVLTHGGQYVQFDIFGNFEEITT
Consensus          MDGAPVAEFRPTMTHGGR LLY IFGN FE T
                            I                              II
OsMAPK5a    KYQPPIMPIGRGAYGIVCSVMNFETREMVAIKKIANAFNN
OsMAPK5b    KYQPPIMPIGRGAYGIVCSVMNFETREMVAIKKIAN----
TaWCK-1     KYQPPIMPIGRGAYGIVCSVMNFETREMVASKKIANAFDN
NtWIPK      KYRPPIMPIGRGAYGIVCSVLNTELNEMVAVKKIANAFDI
Consensus   KYQPPIMPIGRGAYGIVCSVMNFETREMVAIKKIANAF N
                  III            IV
OsMAPK5a    DMDAKRTLREIKLLRHLDHENIIGIRDVIPPPIPQAFNDV
OsMAPK5b    ----------------------------------------
TaWCK-1     NMDAKRTLREIKLLRHLDHENIVGLRDVIPPAIPQSFNDV
NtWIPK      YMDAKRTLREIKLLRHLDHENVIGLRDVIPPPLRREFSDV
Consensus    MDAKRTLREIKLLRHLDHENIIGLRDVIPP IP  FNDV
                         V
OsMAPK5a    YIATELMDTDLHHIIRSNQELSEEHCQYFLYQILRGLKYI
OsMAPK5b    ----------------------------------------
TaWCK-1     YIATELMDTDLHHIIRSNQELSEEHCQYFLYQLLRGLKYI
NtWIPK      YIATELMDTDLHQIIRSNQGLSEDHCQYEMYQLLRGLKYI
Consensus   YIATELMDTDLHHIIRSNQELSEEHCQYFLYQLLRGLKYI
                   VI                  VII
OsMAPK5a    HSANVIHRDLKPSNLLLNANCDLKICDFGLARPSSESDMM
OsMAPK5b    -------------------CDLKICDFGLARPSSESDMM
TaWCK-1     HSANVIHRDLKPSNLLLNANCDLKICDFGLARPSSESDMM
NtWIPK      HSANVLHRDLKPSNLLVNANCDLKICDFGLARPNIENENM
Consensus   HSANVIHRDLKPSNLLLNANCDLKICDFGLARPSSESDMM
                * *        VIII             IX
OsMAPK5a    TEYVVTRWYRAPELLLNSTDYSAAIDVWSVGCIFMELINR
OsMAPK5b    TEYVVTRWYRAPELLLNSTDYSAAIDVWSVGCIFMELINR
TaWCK-1     TEYVVTRWYRAPELLLNSTDYSAAIDVWSVGCIFMELINR
NtWIPK      TEYVVTRWYRAPELLLNSSDYTAAIDVWSVGCIFMELMNR
Consensus   TEYVVTRWYRAPELLLNSTDYSAAIDVWSVGCIFMELINR
                                X
OsMAPK5a    QPLFPGRDHMHQMRLITEVIGTPTDDELGFIRNEDARKYM
OsMAPK5b    QPLFPGRDHMHQMRLITEVIGTPTDDELGFIRNEDARKYM
TaWCK-1     APLFPGRDHMHQMRLITEVIGTPTDDDLGFIRNEDARRYM
NtWIPK      KPLFGGKDHVHQIRLLTELLGTPTEADIGFLQNEDAKRYI
Consensus    PLFPGRDHMHQMRLITEVIGTPTDD LGFIRNEDARKYM
                                                 XI
OsMAPK5a    RHLPQYPRRTFASMFPRVQPAALDLIERMLTFNPLQRITV
OsMAPK5b    RHLPQYPRRTFASMFPRVQPAALDLIERMLTFNPLQRITV
TaWCK-1     RHLPQFPRRSFPGQFPKVQPAALDLIERMLTFNPLQRITV
NtWIPK      RQLPQHPRQQLAEVFPHVNPLAIDLVDKMLTFDPTRRITV
Consensus   RHLPQ PRRTFAS FP VQPAALDLIERMLTFNPLQRITV OsMAPK5a    EEALDHPYLERLHDIADEPICLEPFSFDFEQKALNEDQMK
OsMAPK5b    EEALDHPYLERLHDIADEPICLEPFSFDFEQKALNEDQMK
TaWCK-1     EEALEHPYLERLHDVADEPICTDPFSFDFEQHPLTEDQMK
NtWIPK      EEALDHPYIAKLHDAGDEPICPVPFSFDFEQQGIGEEQIK
Consensus   EEALDHPYLERLHD ADEPIC  PFSFDFEQ  L EDQMK OsMAPK5a    QLIFNEAIEMNPNIRY
OsMAPK5b    QLIFNEAIEMNPNIRY
TaWCK-1     QLIFNEALELNPNFRY
NtWIPK      DMIYQEALSLNPEYA-
Consensus   QLIFNEA E NPN RY
```

B

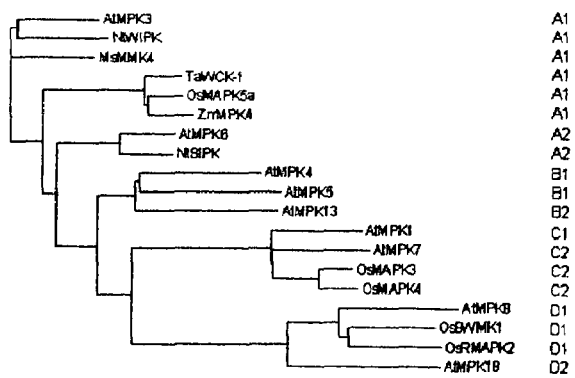

FIGURE 1

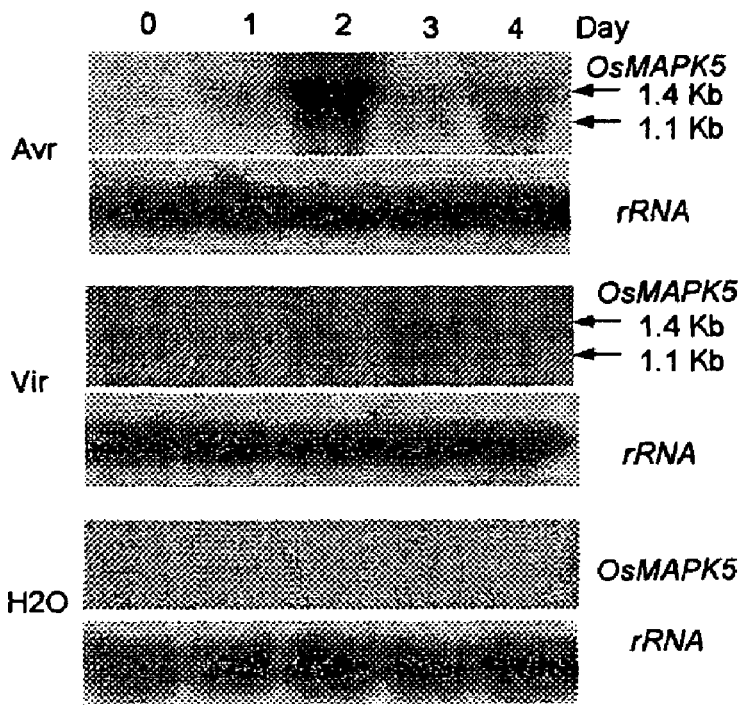
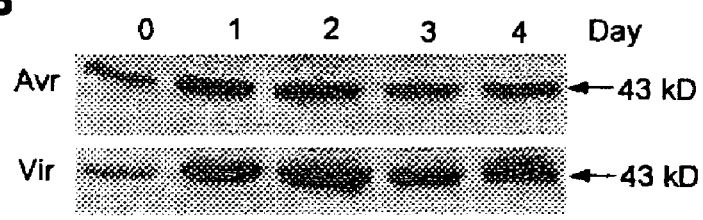
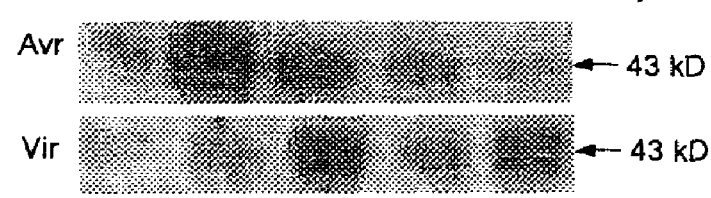
FIGURE 3

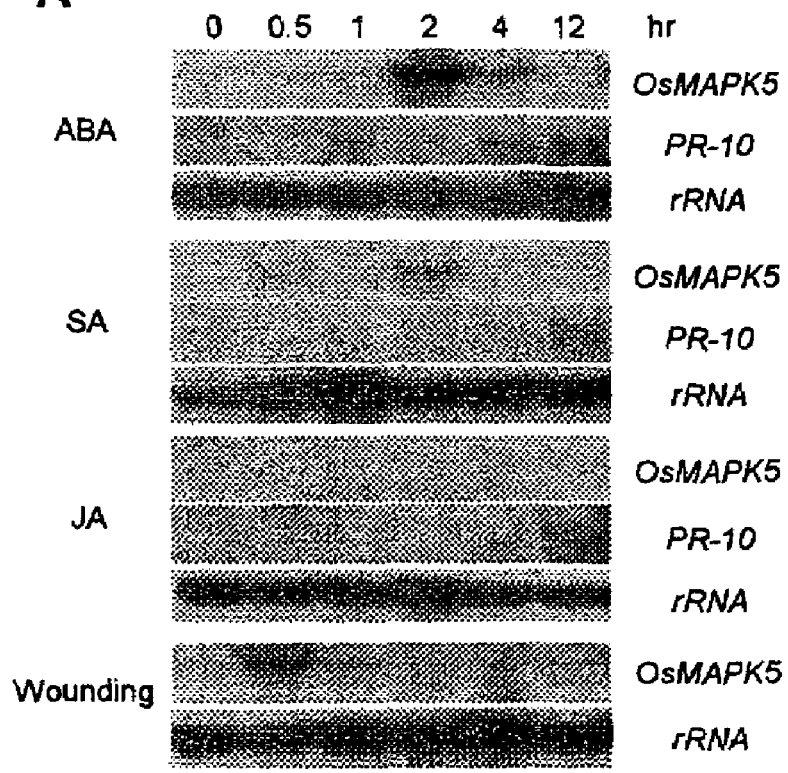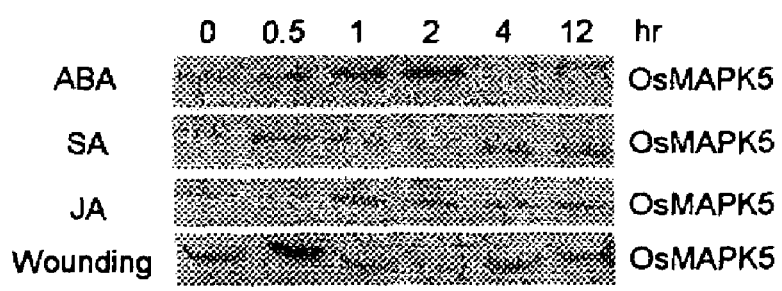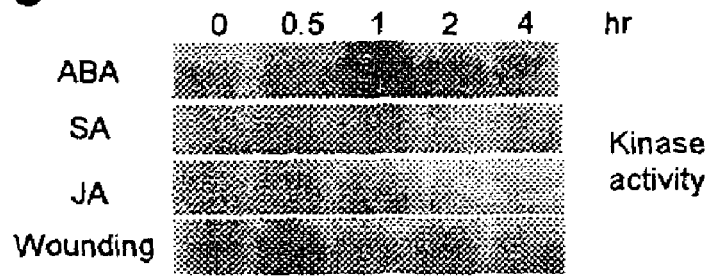
FIGURE 4

A
Drought
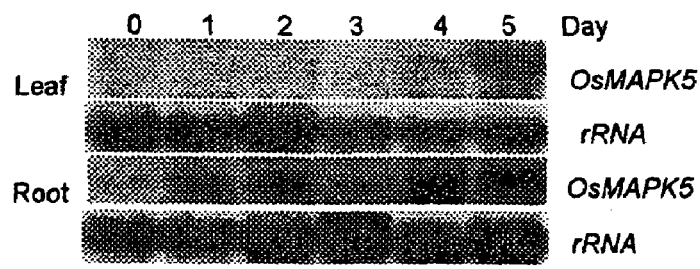
Salinity
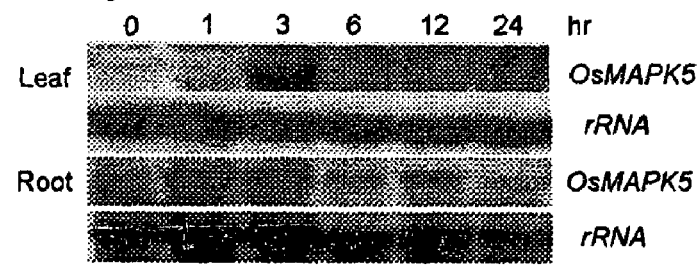
Cold
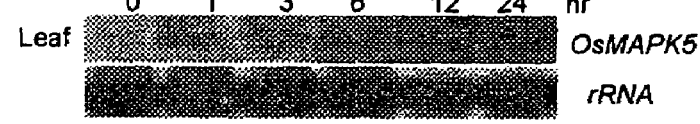
B
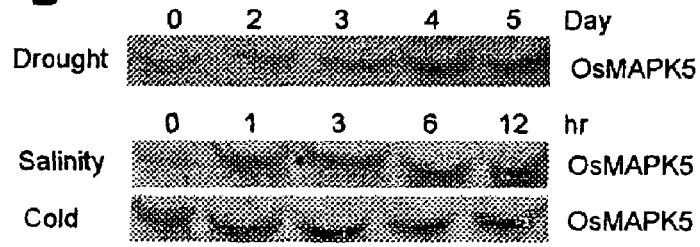
C
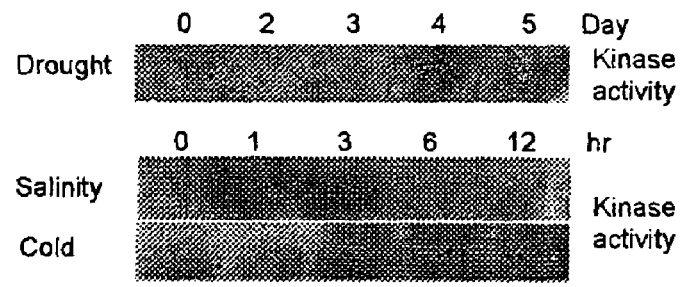
FIGURE 5

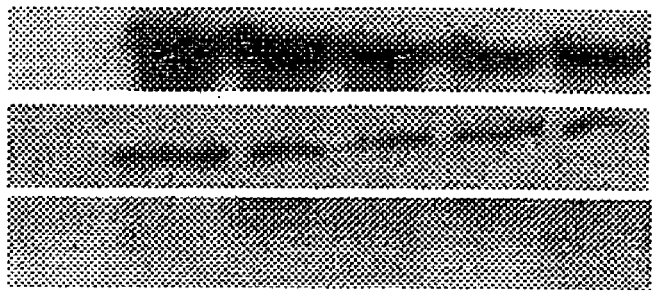
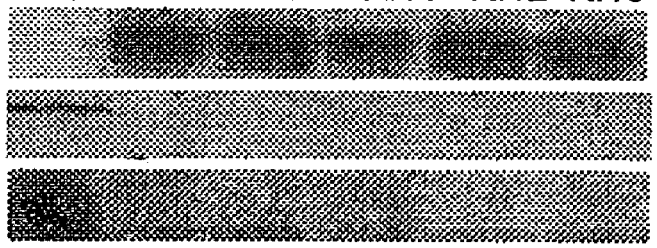
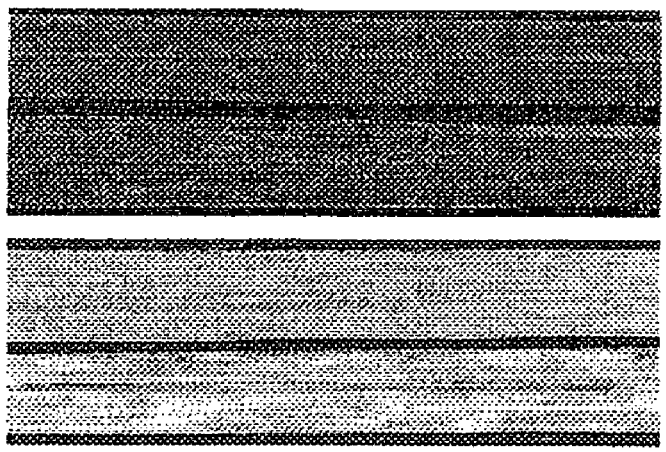
FIGURE 6

A
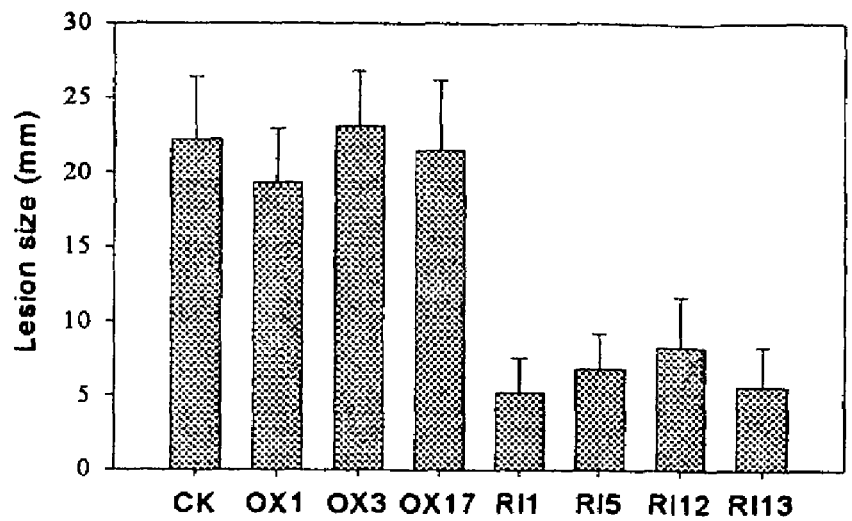
B
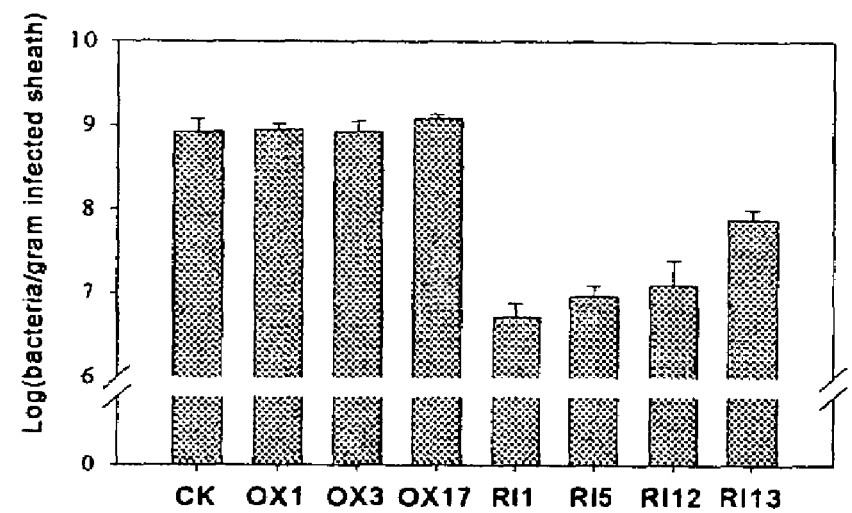
C
FIGURE 8

A
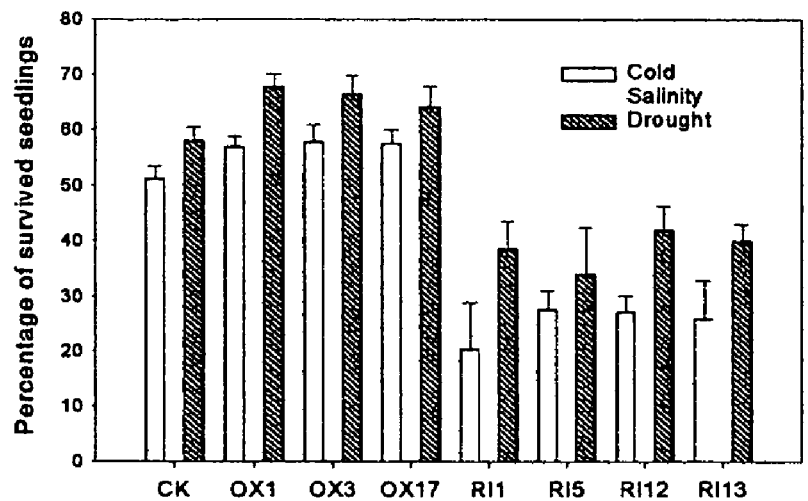
B
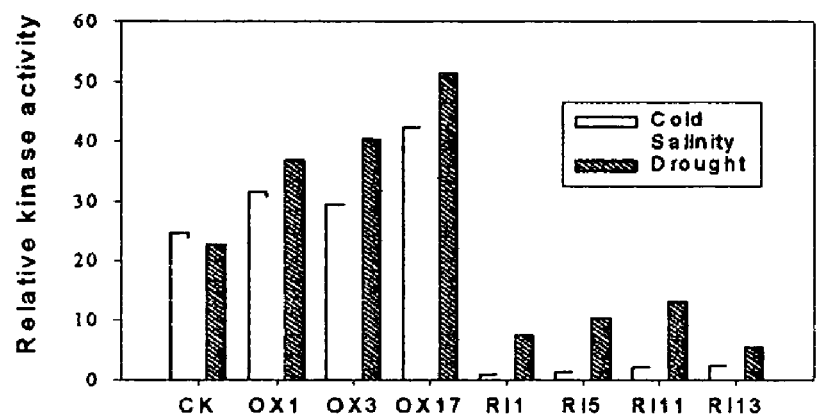
FIGURE 10

OsMAPK5a
SEQ. ID. NO: 1

```
   1    agagagtcag ataaggtcgt taattaggtt ggtcaattcg gctgcttgcg gcgagagaag
  61    aggaggaggg attagggatg gacggggcgc cggtggcgga gttcaggccg acgatgacgc
 121    acggcggccg gtacctgctc tacgacatct cgggaacaa  gttcgaggtg acgaacaagt
 181    accagccgcc catcatgccc attggccgcg gcgcctacgg gatcgtctgc tccgtgatga
 241    actttgagac gagggagatg gtggcgataa agaagatcgc caacgcgttc aacaacgaca
 301    tggacgccaa gcgcacgctc cgggagatca agctcctcag gcacctcgac cacgagaaca
 361    tcataggcat cagggatgtg atcccgccgc cgatccctca ggcgttcaac gacgtctaca
 421    tcgccacgga gctcatggac accgacctcc atcacatcat ccgctccaac aagaactgt
 481    cagaagagca ctgccagtat ttcctgtacc agatcctgcg ggggctcaag tacatccact
 541    cggcgaacgt gatccaccgc gacctgaagc cgagcaacct gctgctgaac gccaactgcg
 601    acctcaagat ctgcgacttc gggctggcgc ggccgtcgtc ggagagcgac atgatgacgg
 661    agtacgtggt cacccggtgg taccgcgcgc cggagctgct gctcaactcc accgactact
 721    ccgccgccat cgacgtctgg tccgtcggct gcatcttcat ggagctcatc aaccgccagc
 781    cgctcttccc cggcagggac cacatgcacc agatgcgcct catcaccgag gtgatcggga
 841    cgccgacgga cgacgagctg gggttcatac ggaacgagga cgcgaggaag tacatgaggc
 901    acctgccgca gtacccgcgc cggacgttcg cgagcatgtt cccgcgggtg cagcccgccg
 961    cgctcgacct catcgagagg atgctcacct caacccgct  gcagagaatc acagttgagg
1021    aggcgctcga tcatccttac ctagagagat tgcacgacat cgccgatgag cccatctgcc
1081    tggagccctt ctccttcgac ttcgagcaga aggctctaaa cgaggaccaa atgaagcagc
1141    tgatcttcaa cgaagcgatc gagatgaacc caaacatccg gtactagatt gaatcaccat
1201    ggaaatgaga tcccgtctat acctgctttg tacatatgat caagattgag agccgggtag
1261    actgaacatt gcatttgttt gtttgttgat gttcgaaacc cacattctct gcaagttgtg
1321    gctgctttgt atgatatatg gtactatgtt cgaataaaag ggtttggaac tttggattaa
1381    aaaaaaaaaa aaaaaa
```

FIGURE 11

OsMAPK5a
SEQ. ID. NO: 2

MDGAPVAEFRPTMTHGGRYLLYDIFGNKFEVTNKYQPPIMPIGR

GAYGIVCSVMNFETREMVAIKKIANAFNNDMDAKRTLREIKLLRHLDHENIIGIRDVI

PPPIPQAFNDVYIATELMDTDLHHIIRSNQELSEEHCQYFLYQILRGLKYIHSANVIH

RDLKPSNLLLNANCDLKICDFGLARPSSESDMMTEYVVTRWYRAPELLLNSTDYSAAI

DVWSVGCIFMELINRQPLFPGRDHMHQMRLITEVIGTPTDDELGFIRNEDARKYMRHL

PQYPRRTFASMFPRVQPAALDLIERMLTFNPLQRITVEEALDHPYLERLHDIADEPIC

LEPFSFDFEQKALNEDQMKQLIFNEAIEMNPNIRY

FIGURE 12

OsMAPK5b

SEQ. ID. NO: 3

```
1     agagagtcag ataaggtcgt taattaggtt ggtcaattcg gctgcttgcg gcgagagaag
61    aggaggaggg attagggatg gacggggcgc cggtggcgga gttcaggccg acgatgacgc
121   acggcggccg gtacctgctc tacgacatct cgggaacaa  gttcgaggtg acgaacaagt
181   accagccgcc catcatgccc attggccgcg gcgcctacgg gatcgtctgc tccgtgatga
241   actttgagac gagggagatg gtggcgataa agaagatcgc caactgcgac ctcaagatct
301   gcgacttcgg gctggcgcgg ccgtcgtcgg agagcgacat gatgacggag tacgtggtca
361   cccggtggta ccgcgcgccg gagctgctgc tcaactccac cgactactcc gccgccatcg
421   acgtctggtc cgtcggctgc atcttcatgg agctcatcaa ccgccagccg ctcttccccg
481   gcagggacca catgcaccag atgcgcctca tcaccgaggt gatcgggacg ccgacggacg
541   acgagctggg gttcatacgg aacgaggacg cgaggaagta catgaggcac ctgccgcagt
601   acccgcgccg gacgttcgcg agcatgttcc cgcgggtgca gcccgccgcg ctcgacctca
661   tcgagaggat gctcaccttc aacccgctgc agagaatcac agttgaggag gcgctcgatc
721   atccttacct agagagattg cacgacatcg ccgatgagcc catctgcctg gagcccttct
781   ccttcgactt cgagcagaag gctctaaacg aggaccaaat gaagcagctg atcttcaacg
841   aagcgatcga gatgaaccca aacatccggt actagattga atcaccatgg aaatgagatc
901   ccgtctatac ctgctttgta catatgatca agattgagag ccgggtagac tgaacattgc
961   atttgtttgt tgttgatgt  tcgaaaccca cattctctgc aagttgtggc tgctttgtat
1021  gatatatggt actatgttcg aataaaaggg tttggaactt tggattaaaa aaaaaaaaaa
1081  aaaa
```

FIGURE 13

OsMAPK5b

SEQ. ID. NO: 4

MMDGAPVAEFRPTMTHGGRYLLYDIFGNKFEVTNKYQPPIMPIGR

GAYGIVCSVMNFETREMVAIKKIANCDLKICDFGLARPSSESDMMTEYVVTRWYRAPE

LLLNSTDYSAAIDVWSVGCIFMELINRQPLFPGRDHMHQMRLITEVIGTPTDDELGFI

RNEDARKYMRHLPQYPRRTFASMFPRVQPAALDLIERMLTFNPLQRITVEEALDHPYL

ERLHDIADEPICLEPFSFDFEQKALNEDQMKQLIFNEAIEMNPNIRY

FIGURE 14

SEQUENCE LISTING

<160> NUMBER OF SEQ ID NOS: 8

<210> SEQ ID NO 1
<211> LENGTH: 1396
<212> TYPE: DNA
<213> ORGANISM: Oryza sativa

<400> SEQUENCE: 1
agagagtcag ataaggtcgt taattaggtt ggtcaattcg gctgcttgcg gcgagagaag    60

```
aggaggaggg attagggatg gacggggcgc cggtggcgga gttcaggccg acgatgacgc      120
acggcggccg gtacctgctc tacgacatct tcgggaacaa gttcgaggtg acgaacaagt      180
accagccgcc catcatgccc attggccgcg gcgcctacgg gatcgtctgc tccgtgatga      240
actttgagac gagggagatg gtggcgataa agaagatcgc caacgcgttc aacaacgaca      300
tggacgccaa gcgcacgctc cgggagatca agctcctcag gcacctcgac cacgagaaca      360
tcataggcat cagggatgtg atcccgccgc cgatccctca ggcgttcaac gacgtctaca      420
tcgccacgga gctcatggac accgacctcc atcacatcat ccgctccaac caagaactgt      480
cagaagagca ctgccagtat tcctgtacc agatcctgcg ggggctcaag tacatccact      540
cggcgaacgt gatccaccgc gacctgaagc cgagcaacct gctgctgaac gccaactgcg      600
acctcaagat ctgcgacttc gggctggcgc ggccgtcgtc ggagagcgac atgatgacgg      660
agtacgtggt cacccggtgg taccgcgcgc cggagctgct gctcaactcc accgactact      720
ccgccgccat cgacgtctgg tccgtcggct gcatcttcat ggagctcatc aaccgccagc      780
cgctcttccc cggcagggac cacatgcacc agatgcgcct catcaccgag gtgatcggga      840
cgccgacgga cgacgagctg ggggttcatac ggaacgagga cgcgaggaag tacatgaggc      900
acctgccgca gtaccgcgc cggacgttcg cgagcatgtt cccgcgggtg cagcccgccg      960
cgctcgacct catcgagagg atgctcacct tcaacccgct gcagagaatc acagttgagg     1020
aggcgctcga tcatccttac ctagagagat gcacgacat cgccgatgag cccatctgcc     1080
tggagccctt ctccttcgac ttcgagcaga aggctctaaa cgaggaccaa atgaagcagc     1140
tgatcttcaa cgaagcgatc gagatgaacc caaacatccg gtactagatt gaatcaccat     1200
ggaaatgaga tcccgtctat acctgctttg tacatatgat caagattgag agccgggtag     1260
actgaacatt gcatttgttt gtttgttgat gttcgaaacc cacattctct gcaagttgtg     1320
gctgctttgt atgatatatg gtactatgtt cgaataaaag ggtttggaac tttggattaa     1380
aaaaaaaaaa aaaaaa                                                     1396
```

<210> SEQ ID NO 2
<211> LENGTH: 368
<212> TYPE: PRT
<213> ORGANISM: Oryza sativa

<400> SEQUENCE: 2

```
Met Asp Gly Ala Pro Val Ala Glu Phe Arg Pro Thr Met Thr His Gly
1               5                   10                  15

Gly Arg Tyr Leu Leu Tyr Asp Ile Phe Gly Asn Lys Phe Glu Val Thr
            20                  25                  30

Asn Lys Tyr Gln Pro Pro Ile Met Pro Ile Gly Arg Gly Ala Tyr Gly
        35                  40                  45

Ile Val Cys Ser Val Met Asn Phe Glu Thr Arg Glu Met Val Ala Ile
    50                  55                  60

Lys Lys Ile Ala Asn Ala Phe Asn Asn Asp Met Asp Ala Lys Arg Thr
65                  70                  75                  80

Leu Arg Glu Ile Lys Leu Leu Arg His Leu Asp His Glu Asn Ile Ile
                85                  90                  95

Gly Ile Arg Asp Val Ile Pro Pro Ile Pro Gln Ala Phe Asn Asp
            100                 105                 110

Val Tyr Ile Ala Thr Glu Leu Met Asp Thr Asp Leu His His Ile Ile
        115                 120                 125
```

```
Arg Ser Asn Gln Glu Leu Ser Glu Glu His Cys Gln Tyr Phe Leu Tyr
    130                 135                 140

Gln Ile Leu Arg Gly Leu Lys Tyr Ile His Ser Ala Asn Val Ile His
145                 150                 155                 160

Arg Asp Leu Lys Pro Ser Asn Leu Leu Asn Ala Asn Cys Asp Leu
                165                 170                 175

Lys Ile Cys Asp Phe Gly Leu Ala Arg Pro Ser Ser Glu Ser Asp Met
            180                 185                 190

Met Thr Glu Tyr Val Val Thr Arg Trp Tyr Arg Ala Pro Glu Leu Leu
            195                 200                 205

Leu Asn Ser Thr Asp Tyr Ser Ala Ala Asp Val Trp Ser Val Gly Cys
    210                 215                 220

Ile Phe Met Glu Leu Ile Asn Arg Gln Pro Leu Phe Pro Gly Arg Asp
225                 230                 235                 240

His Met His Gln Met Arg Leu Ile Thr Glu Val Ile Gly Thr Pro Thr
                245                 250                 255

Asp Asp Glu Leu Gly Phe Ile Arg Asn Glu Asp Ala Arg Lys Tyr Met
            260                 265                 270

Arg His Leu Pro Gln Tyr Pro Arg Arg Thr Phe Ala Ser Met Phe Pro
            275                 280                 285

Arg Val Gln Pro Ala Ala Leu Asp Leu Ile Glu Arg Met Leu Thr Phe
290                 295                 300

Asn Pro Leu Gln Arg Ile Thr Val Glu Glu Ala Leu Asp His Pro Tyr
305                 310                 315                 320

Leu Glu Arg Leu His Asp Ile Ala Asp Glu Pro Ile Cys Leu Glu Pro
                325                 330                 335

Phe Ser Phe Asp Phe Glu Gln Lys Ala Leu Asn Glu Asp Gln Met Lys
            340                 345                 350

Gln Leu Ile Phe Asn Glu Ala Ile Glu Met Asn Pro Asn Ile Arg Tyr
            355                 360                 365

<210> SEQ ID NO 3
<211> LENGTH: 1084
<212> TYPE: DNA
<213> ORGANISM: Oryza sativa

<400> SEQUENCE: 3
agagagtcag ataaggtcgt taattaggtt ggtcaattcg gctgcttgcg gcgagagaag     60
aggaggaggg attagggatg gacggggcgc cggtggcgga gttcaggccg acgatgacgc    120
acggcggccg gtacctgctc tacgacatct tcgggaacaa gttcgaggtg acgaacaagt    180
accagccgcc catcatgccc attggccgcg gcgcctacgg gatcgtctgc tccgtgatga    240
actttgagac gagggagatg gtggcgataa agaagatcgc caactgcgac ctcaagatct    300
gcgacttcgg gctggcgcgg ccgtcgtcgg agagcgacat gatgacggag tacgtggtca    360
cccggtggta ccgcgcgccg gagctgctgc tcaactccac cgactactcc gccgccatcg    420
acgtctggtc cgtcggctgc atcttcatgg agctcatcaa ccgccagccg ctcttccccg    480
gcagggacca catgcaccag atgcgcctca tcaccgaggt gatcgggacg ccgacggacg    540
acgagctggg gttcatacgg aacgaggacg cgaggaagta catgaggcac ctgccgcagt    600
acccgcgccg gacgttcgcg agcatgttcc cgcgggtgca gccgccgcg ctcgacctca    660 tcgagaggat gctcaccttc aacccgctgc agagaatcac agttgaggag gcgctcgatc    720
atccttacct agagagattg cacgacatcg ccgatgagcc catctgcctg gagcccttct    780
```

```
ccttcgactt cgagcagaag gctctaaacg aggaccaaat gaagcagctg atcttcaacg      840
aagcgatcga gatgaaccca acatccggt  actagattga atcaccatgg aaatgagatc      900
ccgtctatac ctgctttgta catatgatca agattgagag ccgggtagac tgaacattgc      960
atttgtttgt tgttgatgt  tcgaaaccca cattctctgc aagttgtggc tgctttgtat     1020
gatatatggt actatgttcg aataaaaggg tttggaactt tggattaaaa aaaaaaaaa     1080 aaaa                                                                  1084
```

<210> SEQ ID NO 4
<211> LENGTH: 266
<212> TYPE: PRT
<213> ORGANISM: Oryza sativa

<400> SEQUENCE: 4

```
Met Met Asp Gly Ala Pro Val Ala Glu Phe Arg Pro Thr Met Thr His
1               5                   10                  15
Gly Gly Arg Tyr Leu Leu Tyr Asp Ile Phe Gly Asn Lys Phe Glu Val
                20                  25                  30
Thr Asn Lys Tyr Gln Pro Pro Ile Met Pro Ile Gly Arg Gly Ala Tyr
            35                  40                  45
Gly Ile Val Cys Ser Val Met Asn Phe Glu Thr Arg Glu Met Val Ala
        50                  55                  60
Ile Lys Lys Ile Ala Asn Cys Asp Leu Lys Ile Cys Asp Phe Gly Leu
65                  70                  75                  80
Ala Arg Pro Ser Ser Glu Ser Asp Met Met Thr Glu Tyr Val Val Thr
                85                  90                  95
Arg Trp Tyr Arg Ala Pro Glu Leu Leu Leu Asn Ser Thr Asp Tyr Ser
            100                 105                 110
Ala Ala Ile Asp Val Trp Ser Val Gly Cys Ile Phe Met Glu Leu Ile
        115                 120                 125
Asn Arg Gln Pro Leu Phe Pro Gly Arg Asp His Met His Gln Met Arg
    130                 135                 140
Leu Ile Thr Glu Val Ile Gly Thr Pro Thr Asp Asp Glu Leu Gly Phe
145                 150                 155                 160
Ile Arg Asn Glu Asp Ala Arg Lys Tyr Met Arg His Leu Pro Gln Tyr
                165                 170                 175
Pro Arg Arg Thr Phe Ala Ser Met Phe Pro Arg Val Gln Pro Ala Ala
            180                 185                 190
Leu Asp Leu Ile Glu Arg Met Leu Thr Phe Asn Pro Leu Gln Arg Ile
        195                 200                 205
Thr Val Glu Glu Ala Leu Asp His Pro Tyr Leu Glu Arg Leu His Asp
    210                 215                 220
Ile Ala Asp Glu Pro Ile Cys Leu Glu Pro Phe Ser Phe Asp Phe Glu
225                 230                 235                 240
Gln Lys Ala Leu Asn Glu Asp Gln Met Lys Gln Leu Ile Phe Asn Glu
                245                 250                 255
Ala Ile Glu Met Asn Pro Asn Ile Arg Tyr
            260                 265
```

<210> SEQ ID NO 5
<211> LENGTH: 26
<212> TYPE: DNA
<213> ORGANISM: Artificial
<220> FEATURE:
<223> OTHER INFORMATION: gene-specific primer containing restriction
      site

```
<400> SEQUENCE: 5
cgggatccgt cggctgcatc ttcatg                                              26

<210> SEQ ID NO 6
<211> LENGTH: 25
<212> TYPE: DNA
<213> ORGANISM: Artificial
<220> FEATURE:
<223> OTHER INFORMATION: gene-specific primer containing restriction
      site

<400> SEQUENCE: 6
gctctagatt caatctagta ccgga                                               25

<210> SEQ ID NO 7
<211> LENGTH: 20
<212> TYPE: DNA
<213> ORGANISM: Artificial
<220> FEATURE:
<223> OTHER INFORMATION: gene-specific primer containing restriction
      site

<400> SEQUENCE: 7
gagttcaggc cgacgatgac                                                     20

<210> SEQ ID NO 8
<211> LENGTH: 20
<212> TYPE: DNA
<213> ORGANISM: Artificial
<220> FEATURE:
<223> OTHER INFORMATION: gene-specific primer containing restriction
      site

<400> SEQUENCE: 8
atcggcgatg tcgtgcaatc                                                     20
```

MITOGEN-ACTIVATED PROTEIN KINASE AND METHOD OF USE TO ENHANCE BIOTIC AND ABIOTIC STRESS TOLERANCE IN PLANTS

1. RELATED APPLICATIONS

This application claims the benefit of U.S. Provisional Application Ser. No. 60/444,249 filed Jan. 31, 2003, which is incorporated by reference herein.

2. FIELD OF INVENTION

The present invention relates to an abscisic acid-inducible mitogen-activated protein kinase (MAPK) and the use of MAPK for increasing abiotic stress tolerance and disease resistance in monocots.

3. BACKGROUND OF THE INVENTION

Plants are constantly exposed to a variety of biotic stress such as pathogen infection or insect herbivory and abiotic stresses such as high or low temperatures, drought and salinity. To survive these challenges, plants have developed elaborate mechanisms to detect external signals and manifest adaptive responses with proper physiological and morphological changes (Bohnert et al., 1995). Detection of extracellular stimuli and subsequent activation of defense responses requires a complex interplay of signaling cascades in which reversible protein phosphorylation plays a central role (Yang et al., 1997).

Increasing evidence has shown that the intracellular signaling module, the mitogen-activated protein kinase (MAPK) cascade plays an important role in plant signal transduction related to biotic and abiotic stresses. This phosphorylation cascade typically consists of three functionally interlinked protein kinases: a MAP kinase kinase kinase (MAPKKK), a MAP kinase kinase (MAPKK) and a MAP kinase (MAP kinase). In this phosphorylation module, a MAPKKK phosphorylates and activates a particular MAPKK which in turn phosphorylates and activates a MAPK. Activated MAPK is often imported into the nucleus where it phosphorylates and activates specific downstream signaling components such as transcription factors (Khokhlatchev et al., 1998).

Activation of MAPKs has been observed in plants exposed to pathogens (Suzuki and Shinshi, 1995; Adam et al., 1997; Ligternik et al., 1997; Zhang and Klessig, 1997, 1998b; He et al., 1999), cold (Jonak et al, 11996), and wounding (Seo et al., 1995; Usami et al., 1995; Bogre et al., 1997; Zhang and Kiessig, 1998a; Seo et al., 1999; He et al., 1999). Plant MAPKs can also be activated by fungal elicitors (Suzuki and Shinshi, 1995), salicylic acid (Zhang and Klessig, 1997), jasmonic acid (Seo et al., 1999), and abscisic acid (Knetsch et al., 1996; Burnett et al., 2000; Heimorvaara-Dijkstra et al., 2000). Although, considerable progress has been made in cloning and characterization of plant MAPKKs (Morris et al., 1997; Ichimura et al., 1998a; Hackett et al., 1998; Hardin and Wolniak, 1998; Kiegerl et al., 2000 Yang et al., 2001) and MAPKKKs (Ichimura et al., 1998b; Kovtun et al., 2000; Frye et al., 2001), detailed steps of MAP kinase cascades have yet to be elucidated in any plant species. Upstream MAPKKs for dicot MAPKs such as NtMEK2 for SIPK/WIPK in tobacco (Yang et., 2001), AtMEK1 for AtMPK4 in *Arabidopsis* (Huang et al., 2000), and SIMKK for SIMK in alfalfa (Kiegerl et al., 2000) have been determined. The complete MAP kinase cascade (EKK1), MKK4/MKK5 and MPK3/MPK6 together with its upstream receptor kinase FLS2 and downstream WRKY22/WRKY29 transcription factors was characterized in *Arabidopsis* (Asai et al., 2002). These findings suggest that MAPKs are important signaling components in plant defense responses and that the cascade of a "three-kinase module" is a general mechanism of defense signal transduction among eukaryotic organisms (Ligterink and Hirt 2000).

Recently, protein kinases possessing close sequence similarity to the mammalian MAPKs have been identified in plants (Stone and Walker, 1995; Hirt, 1997; Mizoguchi et al, 1997; Tena et al., 2001; Ahang and Klessig, 2001; Tchimura et al., 2002). However, despite this progress, most characterized plant MAPKs were isolated from dicot model species such as *Arabidopsis* and tobacco and our understanding of the role of MAPK cascades in stress response remains rather limited. Moreover, very few MAPKs have been identified and characterized in economically important monocot species such as rice, maize, wheat or barley. Rice is not only principal food crop for over half of the world's population, but also an excellent model for cereal crops because of its relatively small genome, extensive genetic mapping data, relatively easy transformation and synteny with other cereal genomes. A MAP kinase, OsBWMK1 found in rice leaf was determined to be activated by blast fungus infection and wounding (He et al., 1999) and a stress-responsive rice MAP kinase gene (variously named OsMAPK5, OsMSRMK2, OsMAPK2, OsMAP1 or OsBIMK1) was identified and shown to be induced at the mRNA level by multiple biotic and abiotic stresses (Xiong et al., 2001; Agrawal et al., 2002; Huang et al., 2002: Wen et al., 2002; Song et al., 2002). Plant MAPKs are encoded by a multigene family and play a pivot role in plant growth and development as well as biotic and abiotic stress responses. As a result, functional genomic analysis of the entire MAPK gene family in rice should significantly enhanced our understanding of the MAPK-mediated signaling network in monocots and its effects on agronomically important traits such as yield, quality, pest resistance and abiotic stress tolerance.

Discussion or citation of a reference herein shall not be construed as an admission that such reference is prior art to the present invention.

4. SUMMARY OF THE INVENTION

This invention relates to a phosphorylation protein called mitogen-activated protein kinase (MAPK) and its role in mediating stress responses in plants. Specifically, the present inventors discovered that the rice mitogen-activated protein kinase gene called OsMAPK5 is differentially spliced generating at least two genes. Accordingly, the present invention encompasses the nucleotide sequences that encode the OsMAPK5, including mutants, isoforms, recombinants and fusion proteins.

Prior studies suggested that other plant MAPK genes are induced by abiotic stresses including drought, salinity and low temperature (Jonak et al., 1996, Munnik et al., 1999; Mikolajczk et al., 2000; Berberich et al., 1999; Huang et al., 2002; Agrawal et al., 2002). However, none of these studies revealed any functional analysis or regulatory correlations with abiotic stresses. The present inventors demonstrated for the first time that an abscisic acid inducible rice mitogen activated protein kinase is capable of inversely modulating disease resistance and abiotic stress tolerance. First, overexpression of OsMAPK5 resulted in enhanced plant tolerance to drought, salt and cold stresses. Secondly, suppression of OsMAPK5 reduced abiotic stress tolerance but led to constitutive PR gene expression and increased disease resistance.

Therefore, the present invention further provides methods for evaluating tolerance to abiotic stress or resistance to biotic stress in plants. For example, one method provides for evaluating a plant for tolerance to abiotic stress comprising treating a plant with an abiotic or biotic stress; isolating MAPK5 protein from the plant; detecting for MAPK5 activity; and evaluating the increase or decrease in MAPK5 activity in the plant whereby the increase in MAPK5 activity indicates the plant is tolerant to stress. MAPK5 or its ortholog is isolated by immunoprecipitating the protein with a MAPK5 protein that specifically binds to MAPK5.

This invention also provides methods for enhancing tolerance to abiotic stress or increasing resistance to biotic stress in a plant. These methods include transforming a plant with MAPK5 nucleic acid sequence wherein the MAPK5 protein is expressed in the plant; treating a plant with an abiotic stress; isolating MAPK5 protein from the plant; detecting for MAPK5 activity; and evaluating the increase or decrease in MAPK5 activity in the transformed plant whereby the increase in MAPK5 activity indicates the increase in tolerance to abiotic stress in the transformed plant compared to the wild-type plant The decrease in MAPK5 activity indicates the increase resistance to biotic stress in the transformed plant compared to the wild-type plant.

The present invention also provides kits for screening plants for susceptibility to biotic stress or tolerance to abiotic stress. The kit includes an isolated nucleic acid probe that comprises a label and a nucleotide sequence that encodes a polypeptide consisting essentially of the amino sequence of MAPK5 or its complement and at least one reagent suitable for detecting the presence of a nucleic acid molecule encoding MAPK5 whereby the changes in polymorphic patterns of MAPK5 indicates the plant is susceptible to biotic stress. Another kit of the present invention provides for detecting a plant for tolerance to abiotic stress comprising an antibody that immunospecifically binds to a MAPK5 polypeptide wherein the antibody is labeled and at least one reagent suitable for detecting the presence of MAPK5 whereby the increase or decrease in MAPK5 activity indicates the plant is tolerant to abiotic stress.

5. DETAILED DESCRIPTION OF THE FIGURES

FIG. 1 represents an amino acid sequence comparison of OsMAPK5a and OsMAPK5b with MAPKs from other higher plants. (A) Alignment of deduced amino acid sequences of OsMAPK5a and OsMAPK5b, SEQ. ID. NOs:2 and 4, respectively, with two closely related MAPKs, TaWCK-1 and NtWIPK, SEQ. ID. NOs:9 and 10, respectively. Conserved amino acid residues are listed. The 11 subdomains of the protein kinases are indicated above the sequences by Roman numbers. Threonine (T) and tyrosine (Y), two residues normally phosphorylated for activation of MAP kinases, are marked by asterisks. (B) The phylogenetic relationship of OsMAPK5a and OsMAPK5b with other plant MAPKs.

FIG. 2 represents genomic organization, alternative splicing, recombinant proteins and autophosphorylation activity of OsMAPK5. (A) Southern blot analysis of the OsMAPK5 gene. (B) RT-PCR analysis using a primer pair covering the differentiated regions of the OsMAPK5a and OsMAPK5b cDNAs. Lane 1 shows RT-PCR analysis of two days post infection blast fungus-induced mRNAs from the cultivar Drew. Lanes 2 and 3 represent PCR analysis of OsMAPK5a and OsMAPK5b cDNAs. (C) In vitro expression of OsMAPK5a and OsMAPK5b, and the specificity of the OsMAPK5 antibody. One hundred nanograms of the total protein from E. coli (left lanes) or 10 ng (right lanes) of affinity-purified fusion protein of His-OsMAPK5a and His-OsMAPK5b were separated on 10% SDS-PAGE and detected with the anti-OsMAPK5 antibody. (D) In vivo autophosphorylation assay of affinity-purified fusion proteins, His-OsMAPK5a and His-OsMAPK5b.

FIG. 3 represents activation of OsMAPK5, its protein and kinase activity by inoculation with the blast fungus. Assays were repeated three times using samples from independent experiments. (A) Northern blot analysis of OsMAPK5 expression using the same gene-specific probe used in Southern blot analysis. Equal loading of total RNAs (20 µg per lane) was verified using rice 28S ribosomal RNA as a loading control. (B) Immunoblot analysis of OsMAPK5. (C) MBP in-gel kinase assay. Only the band corresponding to the activity of OsMAPK5a was shown since no activity was detected for OsMAPK5b. Avr and Vir denote avirulent and virulent isolates of the blast fungus, respectively.

FIG. 4 represents induction of OsMAPK5, its protein and kinase activity by ABA and wounding. (A) Northern blot analysis of OsMAPK5 expression in two-week-old seedlings treated with 0.1 mM ABA, 1 mM SA, 0.1 mM JA or wounding. Total RNAs were extracted at the specified time. The same blots were probed with PBZ1 cDNA. (B) Immunoblot analysis of OsMAPK5 in two-week-old seedlings treated with 0.1 mM ABA, 1 mM SA, 0.1 mM JA or wounding. (C) MBP in-gel kinase activity of the immunoprecipitated OsMAPK5 from two-week-old seedlings treated with 0.1 mM ABA, 1 mM SA, 0.1 mM JA or wounding.

FIG. 5 represents induction of OsMAPK5, its protein and kinase activity by drought, salt and low temperature. Experiments were repeated three times by using samples from independent treatments. (A) Northern blot analyses of OsMAPK5 expression in two-week-old seedlings subjected to drought (water withheld up to 5 days); salt (200mM NaCl) or cold (4° C.) stress. (B) Immunoblot analyses of OsMAPK5 under drought (root tissues), salt (root tissues) and cold (leaf tissues) stresses. (C) MBP in-gel kinase activity assay of the immunoprecipitated OsMAPK5 under drought (root tissues), salt (root tissues) and cold (leaf tissues) stresses.

FIG. 6 represents overexpression and suppression of OsMAPK5 in transgenic rice. (A) The overexpression construct (OsMAPK5-OX) under the control of the CaMV 35S promoter introduced into Nipponbare by the Agrobacterium-mediated transformation. Thirty independent $T_0$ transgenic lines were obtained and examined (5 representative lines and control plant, Nipponbare, are shown) for the OsMAPK5 expression and kinase activity under normal growth condition. The base level of endogenous OsMAPK5 in control plants was not detected under the optimal exposure time for detecting the overexpressed OsMAPK5 (see FIGS. 3 and 4). (B) The double-stranded RNA interference construct (OsMAPK5-R1) under the control of the CaMV 35 S promoter introduced into Nipponbare by the Agrobacterium-mediated transformation. Endogenous OsMAPK5 protein levels and kinase activities in the transgenic lines were examined using rice leaves infected with the fungal isolate IC17-18/1 at 3 days after spot-inoculation. (C) Development of brownish stripes on mature flag leaves of OsMAPK5-R1 transgenic lines. Top and bottom represent control and transgenic rice leaves before and after the removal of chlorophyll (overnight soaking in 100% ethanol), respectively.

Figure 7:
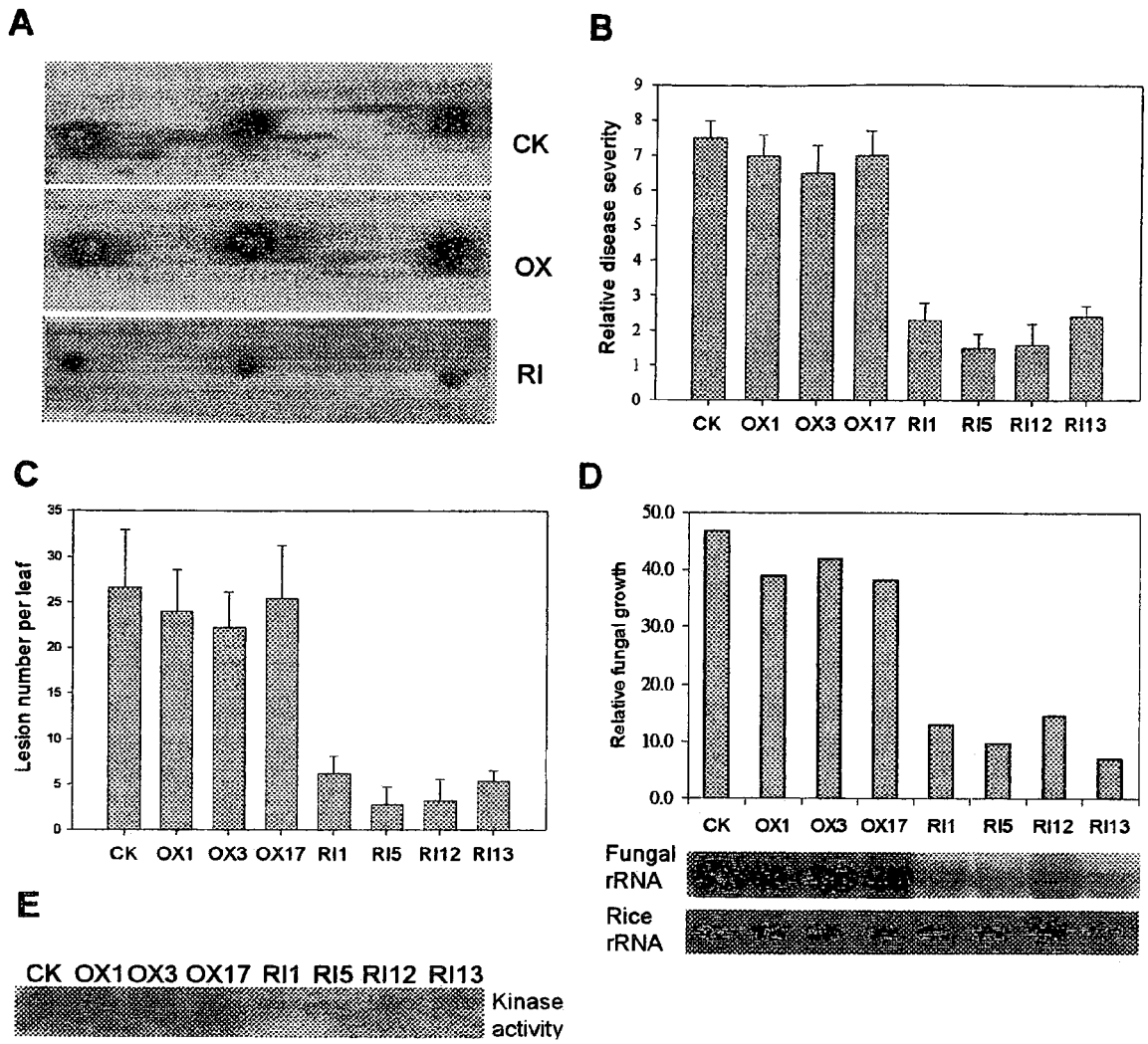

FIG. 7 represents resistance of OsMAPK5-R1 lines to the blast fungus. (A) Blast resistance evaluation of $T_0$ transgenic plants by the spot inoculation method of typical disease symptoms on leaves of control plants and overexpression (OX1) and dsRNAi (RII) transgenic plants at 6 days after inoculation with fungal isolate IC17-18/1. (B) Blast resistance evaluation of two-week-old $T_1$ transgenic plants based on disease rating using 20-40 hygromycin-resistant transgenic seedlings per line from three overexpression lines, four dsRNAi lines and control line were spray-inoculated with fungal isolate IC-18/1. Disease ratings were performed according to Marchetti's scale (Marchetti et al., 1976) at five days post-inoculation. (C) Blast resistance evaluation of $T_1$ transgenic plants based on lesion numbers per infected leaf at five days post-inoculation. (D) Blast resistance evaluation of $T_1$ transgenic plants based on relative fungal growth. Total RNA from infected leaves at five days post-inoculation was blotted and hybridized with *P. grisea* 28S rDNA and rice 25S rDNA respectively. The fungal 28S rDNA hybridization signals were quantified by Phosphoimager and calibrated with rice 25S rDNA signal for equal loading. (E) MBP in-gel kinase assay of the immunoprecipitated OsMAPK5 from leaf tissues of control and transgenic lines at five days post-inoculation.

FIG. 8 represents OsMAPK5-R1 lines resistance to bacterial pathogen, *B. glumae*. Leaf sheaths from one-month-old control and $T_1$ transgenic seedlings were inoculated with *B. glumae* ($1 \times 10^6$ cfu). At least 10 hygromycin-positive transgenic seedlings per line were used in each experiment. (A) Disease resistance evaluation based on lesion size at 7 days post-inoculation. (B) Disease resistance evaluation based on the bacterial growth in planta at 7 days post-inoculation. (C) MBP in-gel kinase assay of immunoprecipitated OsMAPK5 from leaf tissues at 7 days post-inoculation.

Figure 9:
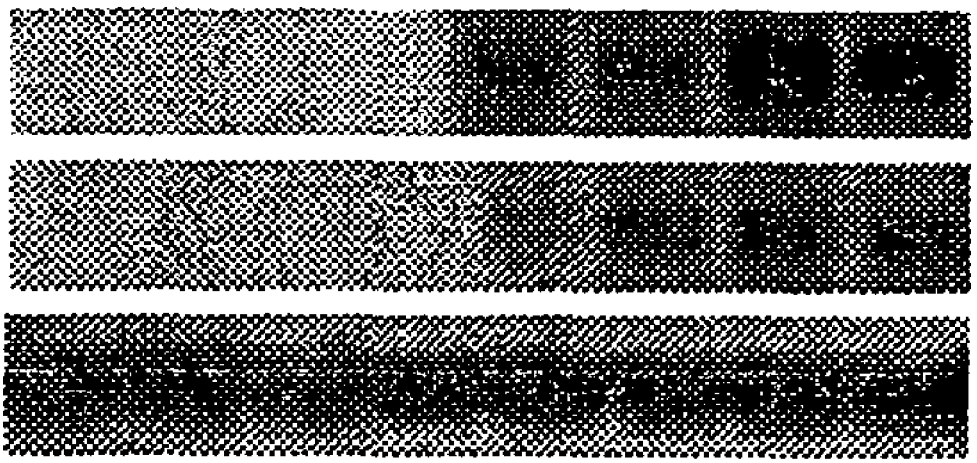

FIG. 9 shows constitutive expression of PR-1 and PR-10 genes in OsMAPK5-R1 transgenic lines. Total RNA was isolated form two-week-old control and $T_1$ transgenic seedlings grown under the normal conditions. The Northern blot was probed sequentially with the PR-1b, PR-10 and rice 25S rDNA with 10 μg of RNA loaded per lane.

FIG. 10 shows tolerance of OsMAPK5-OX and OsMAPK-RI transgenic plants to cold, salt and drought treatments. (A) The percentage of survived seedlings after cold treatment at 4° C. for 3 days followed by normal growth condition for recovery; salt treatment at 200 mM NaCl for a maximum of 4 days; or drought treatment by withholding water for a maximum of 6 days. At least 40 hygromycin-positive $T_1$ transgenic seedlings were used in each experiment and repeated twice. Statistical analysis (t-test) was performed to evaluate the levels of cold, salt and drought tolerance based on the percentage of survived seedlings in the overexpression or suppression lines vsersus the control line after the abiotic treatments. (B) MBP in-gel kinase assay of immunoprecipitated OsMAPK5 from mixed leaf tissues samplings at different times under cold treatment at 6, 12, 24 hours; salinity treatment for 6, 12 and 24 hours or drought treatment for 2, 3, 4 days. The relative MBP kinase activities of control and transgenic lines were calculated based on phosphoimaging quantification of the band intensity.

FIG. 11 represents the nucleic acid sequence of OsMAPKa denoted as SEQ. ID. NO:1.

FIG. 12 represents the amino acid sequence of OsMAPKa denoted as SEQ. ID. NO:2.

FIG. 13 represents the nucleic acid sequence of OsMAPKb denoted as SEQ. ID. NO:3.

FIG. 14 represents the amino acid sequence of OsMAPKb denoted as SEQ. ID. NO:4.

6. DETAILED DESCRIPTION OF THE INVENTION

This section presents a detailed description of the invention and its applications. This description is by way of several exemplary illustrations, in increasing detail and specificity, of the general methods of this invention. These examples are non-limiting, and related variants will be apparent to one of skill in the art.

It should be understood that various changes and modifications to the presently preferred embodiments described herein will be apparent to those skilled in the art. Such changes and modifications can be made without departing from the spirit and scope of the present invention and without diminishing its attendant advantages.

Although, for simplicity, this disclosure often makes references to rice it will be understood by those skilled in the art that the methods of the invention are also useful for the analysis of any plant species.

Mitogen-activated protein kinase (MAPK) plays a crucial role in regulating plant growth and development, as well as abiotic and biotic stress responses. However, until this invention very little was known about MAPK in monocot plants.

The present inventors isolated two alternatively spliced cDNAs, OsMAPK5a and OsMAPKb of a MAP kinase gene from rice. Alternative splicing of hnRNA is an important mechanism of gene expression and regulation.

The OsMAPK5a cDNA is 1396 base pairs (bp) long and encodes a predicted protein of 369 amino acids with an estimated molecular mass of 42.9 kilodaltons (kDa). The OsMAPK5a protein contains 11 subdomains that are conserved among all MAP kinase families (Hirt 1997) and possesses a dual phosphorylation activation motif TEY located between subdomains VII and VIII.

Therefore, the present invention provides an isolated nucleic acid molecule comprising the nucleotide sequence of OsMAPK5a (SEQ. ID. NO: 1). This invention also includes an isolated nucleic acid molecule comprising a nucleotide sequence that encodes a polypeptide consisting of the amino acid sequence of SEQ. ID. NO: 2; or the complement of the nucleotide sequence of a polypeptide consisting of the amino acid sequence of SEQ. ID. NO: 2). The isolated nucleic acid molecule of OsMAPK5a (SEQ ID. NO: 2) includes cDNA or RNA. The present invention further includes an isolated nucleic acid molecule comprising a nucleotide sequence that encodes a polypeptide consisting of substantially the amino acid sequence of SEQ. ID. NO: 2; or the complement of the nucleotide sequence of a polypeptide consisting of substantially the amino acid sequence of SEQ. ID. NO: 2. The phrase "substantially the amino acid sequence" refers to the MAPK5 ortholog of MAPK5 wherein the MAPK5 ortholog is MAPK5 having an identical amino acid sequence, or a polypeptide or polypeptide segment having a similar, non-identical sequence that is considered by those skilled in the art to be a functionally equivalent amino acid sequence. For example, an ortholog MAPK5 gene product having substantially the amino acid sequence of rice MAPK5 can include other monocot MAPK5 genes that are functionally equivalent to rice MAPK5 (SEQ ID NO:2). It is understood that minor modifications of primary amino acid sequence can result in an OsMAPK5-like gene product that has substantially equivalent or enhanced function as compared to the MAPK5 ortholog from which it was derived. Further, various molecules can be attached to an MAPK5 ortholog or active segment thereof, for example, other polypeptides, antigenic or other peptide tags, carbohydrates, lipids, or chemical moieties. Such modifications are included within the term MAPK5 ortholog as defined herein The OsMAPK5b cDNA has an identical nucleotide sequence as that of the OsMAPK5a cDNA but lacks the 312 bp region from position 285 to 596 and encodes an incomplete MAP kinase with the deletion of subdomain III to VI.

The present invention provides also an isolated nucleic acid molecule comprising the nucleotide sequence of MAPK5b (SEQ. ID. NO: 3). The present invention also includes an isolated nucleic acid molecule comprising a nucleotide sequence that encodes a polypeptide consisting of the amino acid sequence of SEQ. ID. NO: 4; or the complement of the nucleotide sequence of a polypeptide consisting of the amino acid sequence of SEQ. ID. NO: 4. The isolated nucleic acid molecule of OsMAPK5b (SEQ. ID. NO: 4) includes cDNA or RNA. The isolated nucleic acid molecule of OsMAPK5b (SEQ ID. NO: 3) includes cDNA or RNA. The present invention further includes an isolated nucleic acid molecule comprising a nucleotide sequence that encodes a polypeptide consisting of substantially the amino acid sequence of SEQ. ID. NO: 4; or the complement of the nucleotide sequence of a polypeptide consisting of the amino acid sequence of SEQ. ID. NO: 4.

Altered nucleotide acid sequences may also be used in accordance with the present invention. Such altered nucleotide acid sequences include deletions, additions or substitutions of different nucleotide residues resulting in a sequence that encodes the same or finally equivalent gene product of the present invention. The gene product itself may contain deletions, additions or substitutions of amino acid residues within the MAPK5 sequences. The DNA sequences of the invention may be engineered to alter the MAPK5 sequences for a variety of ends including, but not limited to alterations which modify processing and expression of the gene product. Mutations may be introduced using techniques well known in the art such as site-directed mutagenesis.

The present inventors generated transgenic rice plants with overexpression using the 35S promoter of Cauliflower mosaic virus and suppression using double-stranded RNA interference (dsRNAi) of OsMAPK5. However, a variety of expression systems may be utilized to express OsMAPK5 or ortholog MAPK5 nucleotide sequences of the present invention. Methods which are well known to those skilled in the art can be used to construct expression vectors containing the OsMAPK5 or ortholog MAPK5 coding sequence and appropriate transcriptional and/or translations control signals. These methods include but are not limited to in vitro recombinant DNA techniques, synthetic techniques and in vivo genetic recombination. Moreover, host cells containing OsMAPK5 or ortholog MAPK5 coding sequence may be identified by nucleic acid hybridization; the presence of or absence of marker genes, or immunoassays for detecting gene products or biological activity.

Therefore, one embodiment of the present invention provides an isolated nucleotide sequence consisting of MAPK5 linked to a heterologous protein or peptide. The present invention further provides recombinant vectors comprising the nucleotide sequence of MAPK5. In one embodiment, the recombinant vectors comprise the nucleotide sequences of OsMAPK5a (SEQ. ID. NO: 1). In another embodiment, the recombinant vectors comprise the nucleotide sequences of OsMAPK5b (SEQ. ID. NO:3).

In yet another embodiment, the present invention provides a recombinant vector comprising an isolated nucleic acid molecule comprising a nucleotide sequence that encodes a polypeptide consisting of substantially the amino acid sequence of SEQ. ID. NO: 2; or the complement of the nucleotide sequence of a polypeptide consisting of the amino acid sequence of SEQ. ID. NO: 2. Another embodiment of the present invention provides a recombinant vector comprising an isolated nucleic acid molecule comprising a nucleotide sequence that encodes a polypeptide consisting of substantially the amino acid sequence of SEQ. ID. NO: 4; or the complement of the nucleotide sequence of a polypeptide consisting of the amino acid sequence of SEQ. ID. NO: 4. It is understood that the complement of OsMAPK5a or OsMAPK5b or ortholog MAPK can be employed in this invention.

This invention includes an expression vector comprising the nucleotide sequence of SEQ. ID. NOs:1 or 2 or ortholog MAPK5 operatively associated with a regulatory nucleotide sequence containing transcriptional and translational regulatory information that controls expression of the nucleotide sequence in a host cell. The host expression vector system may include but not limited to microorganisms, insect, yeast or plants transformed with recombinant expression vectors.

The present invention provides a genetically host cell comprising the nucleotide sequences of SEQ. ID. NOs: 1 or 3 or ortholog MAPK5. The genetically engineered host cell comprises an isolated nucleic acid comprising a nucleotide sequence that encodes a polypeptide consisting of the amino acid sequence of SEQ. ID. NO:2 or the complement of the nucleotide sequence of that encodes a polypeptide consisting of the amino acid sequence of SEQ. ID. NO:2. The genetically engineered host cell comprises an isolated nucleic acid comprising a nucleotide sequence that encodes a polypeptide consisting of the amino acid sequence of SEQ. ID. NO:4 or the complement of the nucleotide sequence of that encodes a polypeptide consisting of the amino acid sequence of SEQ. ID. NO:4. Moreover, the genetically engineered host cell of the present invention includes prokaryotic and eukaryotic cells.

In another embodiment, the genetically engineered host cell comprises the nucleotide sequences of SEQ. ID. NOs: 1 or 3 or ortholog MAPK5 operatively associated with a regulatory sequence containing transcriptional and translational regulatory information that controls expression of the nucleotide sequences in the host cell.

The present invention further provides an isolated nucleic acid comprising a nucleotide sequence that encodes a polypeptide consisting of the amino acid sequence of SEQ. ID. NO:2 or the complement of the nucleotide sequence of that encodes a polypeptide consisting of the amino acid sequence of SEQ. ID. NO:2 operatively associated with a regulatory sequence containing transcriptional and translational regulatory information that controls expression of the nucleotide sequences in the host cell. The present invention further provides an isolated nucleic acid comprising a nucleotide sequence that encodes a polypeptide consisting of the amino acid sequence of SEQ. ID. NO:4 or the complement of the nucleotide sequence of that encodes a polypeptide consisting of the amino acid sequence of SEQ. ID. NO:4 operatively associated with a regulatory sequence containing transitional and translational regulatory information that controls expression of the nucleotide sequences in the host cell. The genetically engineered host cell can be prokaryotic or eukaryotic. The host cell can be a continuous cell line.

This invention also demonstrated that the intact OsMAPK5a isoform has kinase activity. However, neither autophosphorylation nor MBP-kinase activity was detected for the truncated OsMAPK5b isoform. This is not surprising since OsMAPK5b is missing the subdomain VI which contains the catalytic loop of MAP kinase.

Therefore, the present invention provides a MAPK5 polypeptide having kinase activity. In one embodiment, this invention provides a polypeptide which has kinase activity comprising the amino acid sequence of OsMAPK5a (SEQ. ID. NO: 2) or ortholog MAPK. In still another embodiment, the ortholog MAPK polypeptide is selected from the group consisting of monocots or dicots.

The present invention relates to antibodies that are capable of specifically recognizing one or more OsMAPK5 or ortholog MAPK5 gene product epitope. Such antibodies may include but are not limited to polyclonal antibodies, monoclonal antibodies, humanized or chimeric antibodies, single chain antibodies, Fab fragments and epitope-binding fragments of any of the above. Immunoblot analysis using an antibody made against a 140 amino acid fragment of rice MAPK5 reacted with OsMAPK5a and OsMAPK5b.

In a preferred embodiment, the present invention provides an antibody that specifically binds to a peptide consisting of the C-terminal portion of the rice MAPK5 amino acid sequence set forth in SEQ. ID. NO:2. In another embodiment, the invention provides an antibody that specifically binds to a peptide consisting of the C-terminal portion of the rice MAPK5 amino acid sequence consisting of position 763 to the stop codon.

Further, the present invention provides an antibody that specifically binds to a peptide consisting of the C-terminal portion of the rice MAPK5 amino acid sequence set forth in SEQ. ID. NO: 4.

The present inventors detected MAPK protein by utilizing the immunoblotting technique. However, the detecting step of the present invention may be carried out by any suitable immunoassay, including homogeneous assays or heterogeneous assays. Examples of suitable immunoassays include but are not limited to radioimmunoassay, immunofluorescence assay, enzyme-linked immunosorbent assay (ELISA) and immunocytochemical assay.

The present invention provides a method for producing a transgenic plant with a MAPK5 or otholog coding nucleic acid, wherein expression of the nucleic acid in the plant results in increased tolerance to abiotic stress or resistance to biotic stress compared to a wild type plant comprising transforming a plant cell with an expression vector comprising the MAPK5 coding nucleic acid and generating a transgenic plant with an increased tolerance to abiotic stress or increased resistance to biotic stress compared to a wild type plant. In a preferred embodiment of the present invention, Agrobacterium can be employed to introduce the gene constructs into plants.

The present invention provides a transgenic plant transformed with a nucleotide sequence that encodes a MAPK5 or MAPK5 ortholog nucleic acid sequence wherein overexpression of the MAPK5 ortholog nucleic acid sequence in the plant results in increased tolerance to abiotic stress compared to a wild-type plant. In another embodiment, the transgenic plant is transformed by a nucleotide sequence that encodes a polypeptide consisting of the amino acid sequence of SEQ. ID. NO: 2 wherein overexpression of SEQ. ID. NO: 2 in the plant results in increased tolerance to abiotic stress compared to a wild-type plant. Abiotic stress includes but not limited to drought, temperature and salinity.

In yet another embodiment, the transgenic plant is transformed by a nucleotide sequence that encodes RNA interference structure wherein suppression of the MAPK5 ortholog nucleic acid sequence in the plant results in increased resistance to biotic stress compared to a wild-type plant. In still another embodiment, the transgenic plant is transformed by a nucleotide sequence that encodes a polypeptide consisting of the amino acid sequence of SEQ. ID. NO:2 wherein suppression of the expression of SEQ. ID. NO:2 in the plant results in increased resistance to biotic stress as compared to wild-type plant. Biotic stress includes but not limited to infection or disease generated by pathogenic fungi, bacteria, viruses, nematodes and insects.

The present invention further provides a transgenic plant transformed by a nucleotide sequence that encodes a MAPK5 ortholog nucleic acid sequence operatively linked to a regulatory sequence that controls gene expression so that the MAPK5 ortholog nucleic acid sequence is overexpressed in the plant compared to a wild-type plant. In another embodiment, the transgenic plant is transformed by a nucleotide sequence that encodes a polypeptide consisting of the amino acid sequence of SEQ. ID. NO: 2 operatively linked to a regulatory sequence that controls gene expression so that SEQ. ID. NO: 2 is overexpressed in the plant compared to a wild-type plant. The transgenic plant is further transformed by a nucleotide sequence that encodes a MAPK5 ortholog nucleic acid sequence operatively linked to a regulatory sequence that controls gene expression so that expression of the MAPK5 ortholog nucleic acid sequence is suppressed in the plant compared to a wild-type plant.

In another embodiment, the transgenic plant is transformed by a nucleotide sequence that encodes a polypeptide consisting of the amino acid sequence of SEQ. ID. NO: 2 operatively linked to a regulatory sequence that controls gene expression so that expression of SEQ. ID. NO: 2 is suppressed in the plant compared to a wild-type plant.

The transgenic plant of this invention comprises MAPK5 nucleic acid from rice. In another embodiment, the transgenic plant of this invention comprises MAPK5 nucleic acid from a monocot other than rice. Monocots include but not limited to wheat, barley, rice and maize.

The present also includes for seeds produced by the transgenic plants of this invention.

This invention demonstrated for the first time that an ABA-inducible rice MAP kinase is capable of inversely modulating disease resistance and abiotic stress tolerance. On one hand, overexpression of OsMAPK5 resulted in enhanced plant tolerance to drought, salt and cold stresses while on the other hand, suppression of OsMAPK5 reduced abiotic stress tolerance, but led to constitutive PR gene expression and increased disease resistance. Therefore, this invention further provides methods for evaluating tolerance to abiotic stress or resistance to biotic stress. For example, one method provides for evaluating a plant for tolerance to abiotic stress comprising treating a plant with abiotic stress; isolating MAPK5 protein from the plant; detecting for MAPK5 activity; and evaluating the increase or decrease in MAPK5 activity in the plant whereby the increase in MAPK5 activity indicates the plant is tolerant to abiotic stress. Abiotic stress includes infection or disease from pathogenic fungi, bacteria, viruses, nematodes and insects. MAPK5 or its ortholog is isolated by immunoprecipitating the protein with a MAPK5 protein that specifically binds to MAPK5.

In another embodiment, the method of this invention provides for evaluating a plant for resistance to biotic stress comprising treating a plant with a pathogen; isolating MAPK5 protein from the plant; detecting for MAPK5 activity; and evaluating the increase or decrease in MAPK5 activity in the plant whereby the decrease in MAPK5 activity indicates the plant is tolerant to the pathogen. Biotic stress includes drought, temperature and salinity.

In yet another embodiment, the method of this invention provides for enhancing tolerance to abiotic stress in a plant comprising transforming a plant with MAPK5 nucleic acid sequence wherein the MAPK5 protein is expressed in the plant; treating a plant with an abiotic stress; isolating MAPK5 protein from the plant; detecting for MAPK5 activity; and evaluating the increase or decrease in MAPK5 activity in the transformed plant whereby the increase in MAPK5 activity indicates the increase in tolerance to abiotic stress in the transformed plant compared to the wild-type plant.

The studies using the present invention demonstrated that rice PR genes such as PR-1b and PR-10, which are involved in disease resistance, were constitutively activated in both young seedlings and mature OsMAPK5-R1 transgenic lines under normal growth condition. In still another embodiment, the method of this invention provides for increasing resistance to biotic stress in a plant comprising transforming a plant with MAPK5 nucleic acid sequence wherein the MAPK5 protein is expressed in the plant; treating a plant with a biotic stress; isolating MAPK5 protein from the plant; detecting for MAPK5 activity; and evaluating the increase or decrease in MAPK5 activity in the transformed plant whereby the decrease in MAPK5 activity indicates the increase resistance biotic stress in the transformed plant compared to the wild-type plant.

The present also provides kits for screening plants for susceptibility to biotic stress or tolerance to abiotic stress. One kit includes an isolated nucleic acid probe that comprises a label and (a) nucleotide sequence that encodes a polypeptide consisting essentially of the amino sequence of SEQ. ID. NO:2 or (b) the complement of (a). In another embodiment, the kit includes an isolated nucleic acid probe that comprises a label and (a) nucleotide sequence that encodes a polypeptide consisting of essentially the amino sequence of SEQ. ID. NO:4 or (b) the complement of (a).

The kit of the present invention provides for screening a plant for susceptibility to biotic stress comprising a nucleic acid probe and at least one reagent suitable for detecting the presence of a nucleic acid molecule encoding MAPK5 whereby the changes in polymorphic patterns of MAPK5 indicates the plant is susceptible to biotic stress.

Another kit of the present invention provides for detecting a plant for tolerance to abiotic stress comprising an antibody that immunospecifically binds to a MAPK5 polypeptide wherein the antibody is labeled; and at least one reagent suitable for detecting the presence of MAPK5 whereby the increase or decrease in MAPK5 activity indicates the plant is tolerant to abiotic stress.

The following examples are given for the purpose of illustrating various embodiments of the invention and are not meant to limit the present invention.

7. MATERIALS AND METHODS

7.1 Isolation and Sequence Analysis of OsMAPK5

A full-length OsMAPK5 cDNA was isolated using a 231 base pair OsMAPK5 cDNA fragment (JB113) as a probe (Xiong et al., 2001). Approximately 106 plagues from a blast-induced cDNA library (Lee et al. 2001) were screened. The resulting positive clones carrying OsMAPK5 cDNAs were excised in vivo from the lambda ZAP express vector with the aid of ExAssist helper phage (Startagene, La Jolla, Calif.). The full-length OsMAPK5 cDNA clones were sequenced from both directions by a primer walking approach. Automated sequencing service was provided by the University of Arkansas for Medical Science. Sequence analysis was performed using Vector NT1 Suite (Informax, North Bethesda, Md.) and BLAST (Altschul et al., 1990).

7.2 Gene Construction

7.2.1 Construction of OsMAPK5-OX

An overexpression construct, OsMAPK5-OX was constructed by digesting the full length cDNA OsMAPK5 with BamnHI and XbaI and directionally inserting into pCAMBIA1300S, a modified pCAMBIA1300 vector that contains a double CaMV 35S promoter and a terminator.

7.2.2 Construction of OsMAPK5-R1

A doubles-stranded RNA interference (dsRNAi) construct was made by generating antisense and sense fragments of the OsMAPK5 cDNA using restriction enzyme digestions and PCR methods. The antisense fragment spanning nucleotides from 1198 to 1 of OsMAPK5 including 6 bases from the vector of pBK-CMV was obtained by digestion with NcoI and BamHI and inserted into a NcoI and BamHI site of pCMBIA1300S to form an antisense construct, pC1300S-A. The sense fragment spanning nucleotides from 734 to 1198 of OsMAPK5 was generated by PCR with primers B734 containing a BamHI site (5'-CG GGATCCGTCGGCTGCATCTTCATG) (SEQ. ID. NO:5) and X1198 containing a XbaI site (5'-GC TCTAGATTCAATCTAGTACCGGA) (SEQ. ID. NO:6). The PCR product was digested by BamHI and XbaI and inserted into the BamHI and XbaI site of pC1300S-A to form the dsRNAi construct, OsMAPK5-RI.

7.3 Transformation

Overexpression and dsRNAi constructs, OsMAPK5-OX and OsMAPK5-R1 were separately introduced into *Agrobacterium tumefaciens* (strain EHA105) by a freeze-thaw method (Hofgen and Willmitzer, 1998). pCAMBIA1300S vector only transformed plants were used as controls. *Agrobacterium tumefaciens* carrying overexpression or dsRNai constructs was grown overnight in AB induction medium (Winans et al., 1988) containing 50 µg/ml hygromycin and 100 µM acetosyringone. Bacterial cells were collected by centrifugation and resuspended in AB induction medium to an $OD_{600}$ of 0.1. The *Agrobacterium tumefaciens* rice transformation was performed according to Hiei et al. (1994) by vigorously growing calli derived from mature embryos of Nipponbare GA3 (*Oryza sativa* L.), a cultivar that is used in the international rice genome sequencing project and relatively easy for transformation.

Although, the present invention employs *Agrobacterium* to introduce gene constructs into plant tissue and cells, one skilled in the art may employ other techniques. Alternatively, recombinant nucleic acid sequences may also be introduced into plants and plant cells by gene transfer and transformation methods including but not limited to, protoplast transformation, electroporation-mediated uptake of naked DNA and electroporation of plant tissues or plant cell transformation through microinjection.

7.4 Plant Material

Transgenic rice plantlets at 5-6 cm in height were transplanted into Scott® Redi-earth and grown at 28° C. in the greenhouse with a 14/10 hour light/dark cycle. The plants were fertilized with 0.5% ammonium sulfate every two weeks until flowering. Self-pollinated seeds from independent transgenic lines were harvested. $T_1$ plants carrying the transgene were selected by germinating seeds on filter paper soaked with 50 µg/ml hygromycin. Non-transgenic seeds of Nipponbare GA3 (*Oryza saliva* L.) did not germinate in the presence of 50 µg/ml hygromycin. Positive $T_1$ plants were confirmed by PCR or Southern analysis using primers or a probe corresponding to the 35S promoter and/or the 5' region of OsMAPK5. Wild-type and transgenic plants of Nipponbare GA3 (*Oryza sativa* L.) cultivar and the U.S. rice cultivar Drew were used for *M. grisea* infection.

7.5 Pathogen Inoculations

The fungal isolates of the IC-17 pathotype of *P. grisea* were used. On cultivar Drew carrying the Pita resistance gene, the IC17-18/1 isolate carrying avrPita is avirulent. However, its race-change mutant IC17-18/1-2, lacking avrPita is virulent (Harp and Correll, 1998). Both isolates are virulent on cultivar Nipponbare. The fungal infection of $T_0$ transgenic plants was carried out using the spot inoculation method (Jin and Valent, 2001). Leaf segments (5-6 cm long) were isolated from the top of the full-expanded leaf and placed in a Petri dish on a circular filter paper soaked with water. Droplets containing about 50 spores in 0.02% Tween-20 were applied to the leaf surface. The Petri dishes were covered and maintained at 24° C. under white light. Visual evaluation of disease systems and quantification of fungal growth were conducted at 5 or 6 days post-inoculation. The fungal infection of two-week-old $T_1$ and $T_2$ transgenic plants was carried out using the typical spray-inoculation method at a concentration of 250,000 spores per ml (Lee et al., 2001). Blast resistance was evaluated based on the fungal growth in planta (Qi and Yang, 2002) as well as lesion number and size.

Control and transgenic plants were inoculated with a virulent strain of *Burkholderia* glumae, the casual agent of bacterial sheath rot or panicle blight diseases by injecting 20 µl of bacterial suspension (ca. $10^6$ cfu/ml) into sheaths of one-moth-old rice plants. Host resistance to bacterial infection was evaluated based on the severity of disease symptoms as well as the levels of bacterial growth in planta.

7.6 Chemical and Abiotic Treatments

Chemical treatments were conducted on two-week-old seedlings by spraying with abscisic acid (ABA) (0.1 mM), jasmonic acid (JA) (0.1 mM) or salicyclic acid (SA) (1 mM) solutions. Mechanical wounding was achieved by crushing rice leaves with a hemostat.

Abiotic treatments and evaluations were conducted according to Saijo et al (2000). Seedlings were grown in large flat trays rather than individual pots to minimize potential variations among different pots.

Cold stress treatment was performed by transferring seedlings to 4° C. for 3 days and returning to normal growth conditions for recovery.

Drought stress was obtained by withholding water for up to 6 days. Using greenhouse conditions of 28° C. on a 14 h/8 h light/dark cycle and two week old seedlings, leaves began to wilt three days after the free water was removed.

Salt stress treatment was performed by immersing roots of two week old seedlings in 200 mM NaCl solution for up to 4 days. The stressed plants were returned back to normal growth conditions when approximately half of the control plant became wilted. The levels of cold, drought or salt tolerance were evaluated based on the percentage of survived seedlings after a period of recovery.

7.7 Southern and Northern Blot Analysis

Four micrograms of genomic DNA isolated by the CTAB method (Zhang et al., 1992) from the cultivar Drew were digested individually with EcoRI, HindIII, PstI and XbaI; fractionated on a 0.7% agarose gel and blotted onto a nylon membrane (Sambrook et al., 1989). Total RNA was isolated from rice leaves using TRIzol reagent (Life Technologies, Rockville, Md.). Fifteen micrograms of total RNA from each sample were separated on a 1.2% agarose gel containing formaldehyde and then transferred onto a nylon membrane. DNA and RNA ladders (Promega) were added in the gels to estimate the sizes of hybridized bands. DNA or RNA blots were hybridized with a $[\alpha-^{32}P]$ dCTP-labeled gene-specific probe of the sequence from the $999^{th}$ nucleotide to the 3'-end of OsMAPK5a cDNA in PerfectHyb buffer (Sigma). Hybridization and washing conditions were based on the manufacturer's instructions.

Two gene-specific primers, 5'-GAGTTCAGGCCGAC-GATGAC-3' (RT-F99) (SEQ. ID. NO:7) and 5'-ATCGGC-GATGTCGT GCAATC-3' (RT-R1067) (SEQ. ID. NO:8), were designed for amplifying DNA fragments covering the differentiated region of OsMAPK5a and OsMAPK5b transcripts. Rice genomic DNA and reversely transcribed cDNAs from the blast fungus-induced total RNA (two days after infection) were used as templates for the Polymerase Chain Reaction (PCR) analysis.

7.8 Recombinant Protein Production

A BamHI site was introduced to OsMAPK5 at the start codon using Quickchange site-directed mutagenesis (Stratagene). The entire coding region of OsMAPK5 was digested with BamHI and XhoI and ligated in-frame into the His-tag of pET-28(+) vector (Novagen). A specific OsMAPK5 antigen was generated by digesting a DNA fragment spanning from nucleotide positions 763 to the 3'-end of OsMAPK5 with SacI and XhoI and ligating in-frame into the His-tag of pET-28a(+).

7.9 Antibody Production

Recombinant proteins were induced and purified from *E. coli* cells according to the manufacturer's instruction (Pierce). Polyclonal antisera against a 140 amino acid C-terminal region of OsMAPK5 were raised in rats. Antibodies also may be generated from other animals such as but not limited to, rabbits, mice or chickens by known techniques. Antibodies may include, but are not limited to, polyclonal antibodies, monoclonal antibodies, humanized chimeric antibodies, single chain antibodies, Fab fragments and epitope-binding fragments of any of the above.

7.10 Autophosphorylation Assay

The autophosphorylation assay was conducted according to Huang et al. (2000). Purified recombinant OsMAPK5 protein (300 ng) in reaction buffer (40 mM Hepes pH 7.5, 20 mM $MgSO_4$, 10 mM $MnCl_2$, 1 mM $CaCl_2$, 200 mM ATP and 10 µCi $\gamma^{32}P$-ATP) was incubated for 1 hour at room temperature. The reaction mixture was stopped by the addition of SDS sample buffer and heating at 80° C. for 10 minutes. After separation on a 10% SDS-PAGE gel, the phosphorylated product was detected by autoradiography.

7.11 Protein Extraction and Immunoblotting

Rice leaf tissues were ground in liquid nitrogen and homogenized in extraction buffer containing 50 mM Tris (pH 8.0), 1 mM EDTA, 6 mM β-mercaptoethanol, 0.5 mM phenyl-methylsulfonyl fluoride (PMSF) and 0.3 M aprotinin. After centrifugation at 16,000 g, aliquots of supernatant were frozen immediately in liquid nitrogen and stored at −80° C. The protein concentration was determined by using a Bio-Rad protein assay kit with bovine serum albumin (BSA) as a standard.

Equal amounts of protein extracts were separated on 12% SDS polyacrylamide gels and electro-transferred onto nitrocellulose membranes in a transfer buffer (25 mM Tris, 192 mM glycine, 20% methanol, pH 8.3). Non-specific binding sites were blocked by incubating the membrane in 1×TBS-T (25 mM Tris, 140 mM NaCl, 0.1% Tween-20, pH 7.5) containing 6% non-fat dry milk for 1 hour at room temperature. Anti-OsMAPK5 antibody at 1:8000 dilution was added and the membranes were incubated overnight at 4° C. After rinsing 3 times for 15 minutes each with 1×TBS-T, the membrane was incubated with HRP-conjugated anti-rat IgG antibody at 1:1000 dilution (Sigma) in TBS-T buffer for 1 hour at room temperature. Following 5 washes for 15 minutes each with TBS-T buffer, the OsMAPK5 protein was detected with the ECL Plus diction system (Amersham). Biotinylated protein standards were separated in the same gel and detected by Avidin-HRP conjugate (Bio-Rad) as a size marker.

7.12 Immunoprecipitation and In-gel Kinase Activity Assay

Approximately 0.4 milligrams of protein extracts were incubated with 50 μl of anti-OsMAPK5 antibody at 4° C. overnight. Fifty microliters of protein G agarose bead was added and incubated for 2 hours at 4° C. The protein-antibody complex was collected and washed three times in ice-cold phosphate-buffered saline and resuspended in protein sample buffer.

The in-gel kinase activity assay was performed as described by Zhang and Klessig (1997) with some modifications. Forty micrograms of total protein or immunoprecipitate from 400 g of total protein was fractionated on a 10% polyacrylamide gel containing 0.1% SDS and 0.25% mg/ml bovine brain myelin basic protein (MBP, Sigma). SDS was removed by washing the gel three times for 30 minutes each at room temperature with buffer containing 25 mM Tris, pH 7.5, 0.5 mM DTT, 0.1 mM $Na_3VO_4$, 5 mM NaF, 0.5 ma/ml BSA, 0.1% Triton X-100. The kinases were allowed to renature overnight at 4° C. with three changes of renature buffer (25 mM Tris, pH 7.5, 1 mM DTT, 0.1 mM $Na_3VO_4$, 5 mM NaF). The phosphorylation of MBP was performed in a 30 milliliter reaction buffer (25 mM Tris, pH 7.5, 2 mM EGTA, 12 mM $MgCl_2$, 1 mM DTT, 0.1 mM $Na_3VO_4$) with the addition of 0.2 M ATP and 50 μCi $\gamma$-$^{32}$P-ATP (3000 Ci/mmol) at room temperature for 60 minutes. The gel was transferred to washing buffer (5% trichloroacetic acid, 1% sodium pyrophosphate) at room temperature for at least 5 hours with five buffer changes.

8. EXAMPLES

The invention having been described, the following examples are offered by way of illustration and not limitation.

8.1 Isolation and Sequence Analysis of OsMAPK5 cDNAs

A rice cDNA fragment (JB113) was previously identified to be inducible by blast fungus, *M. grisea* (Xiong et al. 2001). Full-length cDNA clones were isolated from a rice cDNA library using the JB113 cDNA fragment as a probe. Two full-length OsMAPK5 cDNAs that are alternatively spliced from a single gene were isolated and designated as OsMAPK5a and OsMAPK5b.

The OsMAPK5a cDNA (accession number AF479883) is 1396 base pairs (bp) long and encodes a predicted protein of 369 amino acids (FIG. 1A) with an estimated molecular mass of 42.9 kilodaltons (kDa). The OsMAPK5a protein contains 11 subdomains that are conserved among all MAP kinase families (Hirt 1997) and possesses a dual phosphorylation activation motif TEY located between subdomains VII and VIII (FIG. 1A). The protein shares the identical amino acid sequence encoded by OsMSRM2 (Agrawal et al., 2002), OsMAPK2 (Huang el., 2002), OsMAP1 (Wen et al., 2002) and OsMIMK1 (Song et al., 2002). The OsMAPK5a protein also shares a very high homology of 91% identity with the elicitor-inducible TaWCK-1 (Takezawa et al., 1999) from wheat and 73% identity with the wound-inducible NtWIPK (Seo et al., 1995) from tobacco.

Phylogenetic analysis based on sequence alignment of the catalytic domain suggests that OsMAPK5a belongs to the A1 subgroup of plant MAP kinase family (FIG. 1B). The phylogenetic relationship of OsMAPK5a and OsMAPK5b was compared to other plant MAPKs. The dendrogram was constructed using Vector NTI Suite software (Informax, North Bethesda, Md.). For simplicity, representatives from the eight subgroups of plant MAPKs, including a few putative rice MAPKs, were included in the dendrogram. The accession numbers for the MAPKs shown in the figure are as follow: AtMPK3, D21839; NtWIPK, D61377; MsMMK4, T09622; TaWCK-1, AF079318; OsMAPK5a, AF479883; ZmMPK4, AB016801; AtMPK6, D21842; NtSIPK, U94192; AtMWK4, D21840; AtMPK5, D21841; AtMPK13, AAF75067; AtMPK1, D14713; AtMPK7, D21843; OsMAPK3, AF216317; OsMAPK4, AJ251330; AtMPK8, AB038693; OsBWMK1, AF177392; OsMAPK2, AF194416. Previous studies indicate that members of the A1 and A2 subgroups are frequently activated by various biotic and abiotic stresses (Zhang and Klessig, 2001).

The OsMAPK5b cDNA (accession number AF479884) has an identical nucleotide sequence as that of the OsMAPK5a cDNA except that a 312 bp region from position 285 to 596 is deleted. The OsMAPK5b encodes an incomplete MAP kinase with the deletion of subdomain III to VI (FIG. 1A).

8.2 Genetic Analysis of OsMAPK5

To determine whether OsMAPK5a and OsMAPK5b were derived from alternative splicing of a single gene, Southern hybridization was performed using a probe covering an identical region of OsMAPK5a and OsMAPK5a (nucleotide 999 to the 3'-end of OsMAPK5a). One strongly hybridizing band was detected in rice genomic DNA digested with EcoRI, HindIII, PstI, and XbaI, respectively (FIG. 2A). Genomic PCR of rice genomic DNA using two primers that covered the differentiated region also gave rise to a single fragment (data not shown). However, RT-PCR with the same pair of primers amplified two cDNA fragments from the blast fungus-induced RNA sample. Molecular sizes of 1.0 and 0.6 kb matched consistent with the predicted sizes of the cDNA fragments based on the location of the two primers (FIG. 2B). Therefore, OsMAPK5a and OsMAPK5b most likely resulted from the alternative splicing of a single OsMAPK5 gene in rice. There is a low-level expression of OsMAPK5 in normal, uninfected leaves, as detected by RT-PCR (data not shown). In both uninfected and infected leaf tissues, OsMAPK5a was a predominant isoform of OsMAPK5 transcripts.

8.3 Analysis of Kinase Activity in OsMAPK5a and OsMAPK5b

To determine whether OsMAPK5a and OsMAPK5b encode active MAP kinases, the recombinant proteins of both OsMAPK5a and OsMAPK5b were produced and purified from *E. coli* cells harboring OsMAPK5a and OsMAPK5b coding sequences in the expression vector pET-28c(+), respectively. As expected, OsMAPK5b was 12 kDa smaller than OsMAPK5a as a result of 312 bp or a 104 amino acid deletion (FIG. 2C). Kinase assays revealed that only OsMAPK5a exhibited autophosphorylation activity, suggesting that the missing subdomains in OsMAPK5b are essential for the kinase activity (FIG. 2D).

8.4 Induction of OsMAPK5 by *M. grisea* Infection

Previous study by the present inventors revealed that OsMAPK5 was inducible by the blast fungus (Xiong et al., 2001). To further assess the expression pattern of OsMAPK5 during fungal infection, an avirulent blast isolate carrying AvrPita and its virulent mutant lacking AvrPita were used to elicit resistant and susceptible reactions, respectively, on rice cultivar Drew, *Oryza sativa* spp. *japonica*, carrying the Pita resistance gene. RNA blots prepared from mock-treated and blast-infected leaves were hybridized with a gene-specific probe of OsMAPK5. Two hybridizing transcripts were determined to be induced by the blast fungus (FIG. 3A). The sizes of the transcripts were similar to those of OsMAPK5a and OsMAPK5b cDNAs at 1.4 and 1.1 Kb, respectively. However, the induced level of OsMAPK5b transcripts was significantly lower than that of OsMAPK5a. In the resistant interaction, the mRNA level of OsMAPK5 was induced as early as one day after inoculation, peaked on the second day and then declined (FIG. 3A). In the susceptible interaction, the transcripts accumulated slowly, but lasted longer than in the resistant interaction. However, the peak level of induced OsMAPK5 was significantly higher in the resistant interaction than in the susceptible interaction. No induction of OsMAPK5 was detected in mock-treated leaves indicating that induction of OsMAPK5 was not due to the effect of spray inoculation (FIG. 3A).

Using anti-OsMAPK5 antibody, a 43 kDa protein corresponding to OsMAPK5a with a predicted size 42.9 kDa was detected in rice leaves infected with *M. grisea* (FIG. 3B). Immunoblot analysis indicated that the level of OsMAPK5a protein increased slightly on the second day after the infection with avirulent isolate and then dropped to the base level. In the susceptible reaction, however, much more protein was induced and the induction lasted longer (FIG. 3B). The OsMAPK5b protein with a predicted size 31.2 kDa was undetectable using the same experimental conditions for detecting OsMAPK5a (5 to 10 min of exposure time using the ECL-Plus detection kit). A rather weak band corresponding to OsMAPK5b was detected under extended exposure time of more than 1 hour. An unknown constitutively expressed protein with a molecular weight of 49 kDa cross-reacted with the anti-OsMAPK5 antibody (data not shown).

To further examine whether the OsMAPK5a kinase activity was induced by blast infection, the endogenous OsMAPK5a was immunoprecipitated and subjected to in-gel kinase assay using myelin basic protein (MBP) as a substrate. Results showed that the OsMAPK5a kinase activity was significantly induced by *P. grisea* infection. In the resistant interaction, the kinase activity increased one day after fungal inoculation and then declined progressively to the base level. In the susceptible interaction, the kinase activity increased after 2 days, but remained moderately high until the final stage of infection (FIG. 3C). Since neither MBP kinase activity (FIG. 3C) nor autophosphorylation activity (FIG. 2D) was detected for OsMAPK5b, only the band corresponding OsMAPK5a was shown in the immunoblot analyses. These data suggest that the early transient activation of OsMAPK5a activity is probably related to the resistance response to avirulent blast isolates. The constant activation of OsMAPK5a in the later stage of infection, on the other hand, may be related to stress resulting from the development of the disease.

8.5 Induction of OsMAPK5 by ABA and Wounding

To determine the effects of different signaling molecules on OsMAPK5 activation, two-week-old rice seedlings were treated with abscisic acid (ABA), salicylic acid (SA) and jasmonic acid (JA). RNA blot analysis revealed that the OsMAPK5a was significantly induced in rice leaves treated with 0.1 mM ABA (FIG. 4A). Transcripts of OsMAPK5a quickly accumulated to the highest level at 2 hours after treatment and then declined. However, OsMAPK5a was only slightly induced, if at all, in leaves treated with 1 mM SA or 0.1 mM JA. Moreover, treatments with higher concentration of SA or JA did not significantly induce OsMAPK5a (data not shown). In contrast, a defense-related gene PR-10 was induced by SA and JA as expected (FIG. 4A). Expression of OsMAPK5a increased significantly in wounded leaves, peaking at 30 min after wounding and then decreasing rapidly to the base level (FIG. 4A). The transcript of OsMAPK5b was not induced by all these chemical treatments or wounding.

Immunoblot analysis revealed that the OsMAPK5 protein was induced by ABA and wounding but not by SA or JA (FIG. 4B). The immunocomplex in-gel kinase assay also revealed that OsMAPK5 activity was induced by ABA and wounding but not by SA or JA (FIG. 4C). After ABA treatment, the peak of OsMAPK5 activity appeared earlier than that of the mRNA and protein. Similar phenomena were also observed following the fungal infection (FIG. 3) or abiotic treatments (FIG. 5). Previously, Seo et al. (1995) reported that the peak of tobacco WIPK activity appeared much earlier than that of its mRNA after mechanical wounding. It is very likely that the basal level OsMAPK5 can be activated very quickly before the accumulation of its mRNA and protein.

8.6 Induction of OsMAPK5 by Drought, Salinity and Low Temperature

RNA blot analysis revealed that OsMAPK5a was induced by drought, salinity or low temperature (FIG. 5A). In the drought and salt treatments, OsMAPK5a was induced earlier in roots or within 1 day and an 1 hour for drought and salinity, respectively than in leaves within 4 days and 3 hours for drought and salinity, respectively. The transcript of OsMAPK5a remained high throughout the course of drought stress. Under salt stress, however, the transcripts declined at 6 hours after the treatment. The transcript of OsMAPK5a was also inducible within 6 hours by low temperature (4° C.) treatment (FIG. 5A).

Immunoblot analyses revealed that the protein level of OsMAPK5 was significantly increased in rice seedlings under drought and salt stresses, but was slightly induced by low temperature (FIG. 5B). Immunocomplex kinase assay indicated that OsMAPK5 activity was also induced by drought, salt and low temperature (FIG. 5C). These results suggest that OsMAPK5 is likely involved in abiotic stress responses in rice plants.

8.7 Overexpression of OsMAPK5 in Transgenic Rice

To clarify the role of OsMAPK5a in biotic and abiotic stress responses, the expression of OsMAPK5 was constitutively increased or suppressed in transgenic rice. The transgenic lines were generated by introducing the overexpression construct, OsMAPK5-OX or the double-stranded RNA interference construct, OsMAPK5-R1 into cultivar Nipponbare GA3.

A total of 30 independent overexpression lines were generated using the OsMAPK5-OX construct. Southern analysis indicated that 19 OsMAPK5-OX lines contained a single-copy insertion (data not shown). RNA blot analysis showed that the OsMAPK5 gene was expressed constitutively in transgenic lines but not in the control plants under normal growth conditions (5 lines are shown in FIG. 6A as examples). As expected, the protein of OsMAPK5a was constitutively produced in the transgenic lines but not in the control plants under normal growth conditions (FIG. 6A). However, the MBP kinase activity of OsMAPK5a in these lines was not significantly increased (FIG. 6A). All the OsMAPK5-OX lines showed no obvious phenotypic changes in comparison with control plants throughout the life cycle.

8.8 Suppression of OsMAPK5 in Transgenic Rice

A total of 38 independent suppression lines were generated using the OsMAPK5—R1 construct. Twenty-four OsMAPK5-R1 lines were confirmed by Southern hybridization to carry a single-copy insertion (data not shown). RNA blot analysis showed that OsMAPK5-R1 construct was constitutively transcribed in suppression lines (5 lines are shown in FIG. 6B as examples). Since the endogenous level of OsMAPK5 in control plants is rather low under normal growth conditions (FIG. 3C), the effectiveness of dsRNAi in $T_0$ transgenic lines was examined after induction of OsMAPK5 by spot inoculation of rice leaves with the blast fungus. Strikingly, the production of endogenous OsMAPK5 protein was almost completely blocked even under the induced condition. In fact, no MBP kinase activity was detected for OsMAPK5 in these transgenic lines (FIG. 6B). The suppression of endogenous OsMAPK5 by dsRNAi was also transmitted to $T_1$ transgenic plants (see Section 7.7). None of the OsMAPK5-R1 lines showed obvious phenotypic changes from germination to the early vegetative growth stage. However, starting from the late vegetative stage of about 2 months after germination, irregular brownish stripes developed on the mature leaves of OsMAPK5-R1 lines (FIG. 6C). Nevertheless, each OsMAPK5-R1 lines proceeded to the reproductive stage and had normal seed setting.

When conducting the in-gel kinase assay using leaf protein extracts from the blast fungus-infected seedlings, kinase activity of a 37 kDa protein was significantly increased in OsMAPK5-R1 transgenic plants but not in the control plants (unpublished data). This data suggests a potential antagonistic effect of OsMAPK5 on an unknown MBP kinase that may positively regulate defense response in rice.

8.9 Negative Regulation of Broad-Spectrum Host Resistance by OsMAPK5

The effects of overexpression or suppression of OsMAPK5 on host resistance to fungal and bacterial pathogens was examined. Disease resistance was initially evaluated on first generation ($T_0$) transgenic lines by spot inoculation of transgenic leaves with a virulent isolate of *M. grisea* because single $T_0$ plants were not suitable for spray inoculation. Both control and OsMAPK5-OX $T_0$ lines exhibited the same level of disease susceptibility to blast infection with the average lesion sizes of 7.0±1.2 mm and 6.8±1.6 mm, respectively. But all OsMAPK5-R1 $T_0$ lines (20 lines tested) exhibited significantly enhanced resistance with average lesion size of 2.8±1.1 mm. Fungal growth that was quantified based on relative rRNA contents of *M. grisea* in inoculated spots was also reduced about three to six fold in OsMAPK5-R1 lines compared to control or OsMAPK5-OX lines.

To confirm the results from the $T_0$ generation, the disease resistance in the second generation ($T_1$) of transgenic rice using three OsMAPK5-OX lines, four OsMAPK5-R1 lines and the control line was evaluated. Due to the transgene segregation in the $T_1$ generation, seedlings carrying the OsMAPK5-OX or OsMAPK5-R1 constructs were first identified based on hygromycin resistance and positive PCR amplification of the transgene. Approximately 40 two-week-old $T_1$ seedlings from each line (a total of more than 320 seedlings) were spay-inoculated with the fungal isolate (IC17-18/1). As indicated by significantly reduced disease severity (FIGS. 7A and 7B), lesion numbers (FIG. 7C) and fungal growth (FIG. 7D), all four OsMAPK5-R1 lines demonstrated increased resistance to blast infection. In contrast, the control and OsMAPK5-OX plants were very susceptible to the same fungal isolate. As expected, the normal induction of OsMAPK5 kinase activity by fungal infection was almost completely suppressed in these OsMAPK5-RNAi lines (FIG. 7E), suggesting that suppression of OsMAPK5 activity likely led to the enhanced resistance.

To test whether OsMAPK5-R1 lines have broad-spectrum resistance to other pathogens, four-week-old $T_1$ plants were infected with *Burkholderia glumae*, a bacterial pathogen causing rice diseases known as panicle blight, glume blight or sheath rot complex (Cottyn et al., 1996). In comparison with the control or OsMAPK5-OX lines, OsMAPK5-R1 lines exhibited significantly elevated resistance against the bacterial pathogen as indicated by reduced lesion size (FIG. 8A) and bacterial growth FIG. 8B). The OsMAPK5 kinase activity was activated by *B. glumae* in both control and OsMAPK5-OX plants but was again suppressed in OsMAPK5-R1 lines (FIG. 8C). These results demonstrate that suppression of OsMAPK5 activity in rice may result in broad-spectrum resistance to fungal and bacterial pathogens.

In all the tests, the control and OsMAPK5-OX plants demonstrated no significant difference in host susceptibility to either *M. gisea* or *B. glumae* (FIGS. 7B and 8B). Although the OsMAPK5 protein was constitutively expressed in the OsMAPK5-OX lines (FIG. 6B), the kinase activity was not significantly increased upon infection by either *M. gisea* or *B. glumae* (FIGS. 7E and 8C). Therefore, the levels of disease resistance appear to correlate with the change of OsMAPK5 kinase activity in rice plants.

8.10 Negative Regulation of PR Gene Expression by OsMAPK5

Since OsMAPK5-R1 lines exhibited elevated resistance to fungal and bacterial pathogens, the expression of some pathogenesis-related (PR) genes in OsMAPK5-OX and OsMAPK5-R1 lines under normal growth conditions. Interestingly, RNA blots showed that two rice PR genes, PR-1b and PR-10, were constitutively expressed in OsMAPK5-R1 $T_1$ transgenic seedlings in the absence of pathogen infection, but not in non-transgenic or OsMAPK5-OX seedlings grown under the same conditions (FIG. 9). Similar results were obtained in $T_0$ transgenic plants and leaf tissues from different developmental stages (data not shown). These data suggest that OsMAPK5 could negatively modulate (probably through an indirect effect) PR gene expression (at least PR-1 and PR-10) as well as broad-spectrum disease resistance.

8.11 Positive Regulation of Drought, Cold and Salt Tolerance by OsMAPK5

The effects of overexpression or suppression of OsMAPK5 on the tolerance of transgenic plants to cold, drought and salt stresses was examined. Stress tolerance was evaluated based on the percentage of seedlings survived after cold, drought or salt treatment. Surprisingly, the four OsMAPK5-R1 lines with enhanced disease resistance exhibited significantly (P<0.001) reduced tolerance to cold, drought and salt stresses (FIG. 10A). In contrast, the three OsMAPK5-OX lines showed significantly increased tolerance to salinity (P<0.005), drought (P<0.01) and cold (P<0.05). The kinase activity of OsMAPK5 in transgenic lines was also assayed after the stress treatments. As expected, the normal activation of OsMAPK5 by cold, salinity and drought was suppressed in OsMAPK5-R1 lines, whereas, the kinase activity in OsMAPK5-OX lines was higher than in control plants (FIG. 10B). These results suggest that the activation of OsMAPK5 positively regulated plant tolerance to abiotic stresses such as drought, salinity and low temperature.

All references cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

REFERENCES

1. Adam, A. L., Pike, S., Hoyos, E., Stone, J. M., Walker, J. C. and Novacky, A. Rapid and transient activation of a myelin basic protein kinase in tobacco leaves treated with harpin from *Erwinia amylovora*. 1997 Plant Physiol. 115:853-861.
2. Agrawal, G>. K., Rakwal, R., and Iwahashi, H. Isolation of novel rice (*Oryza saliva* L.) multiple stress responsive MAP kinase gene, OsMSRMK2, whose mRNA accumulates rapidly in response to environmental cues. 2002 Biochem. Biophys. Res. Commun. 294:1009-1016.
3. Altschul, S. F., Gish, W., Miller, W., Myers, E. W. and Lipman, D. J. Basic local alignment search tool. 1990J. Mol. Biol. 215:403-410.
4. Anderson, P. A., Lawrence, G. J., Morrish, B. C., Ayliffe, M. A., Finnegan, E. J. and Ellis, J. G. Inactivation of the falx rust resistance gene M associated with loss of a repeated unit within the leucine-rich repeat coding region. 1997 Plant Cell 9:641-651.
5. Asai, T., Tena, G., Plotnikova, J., Willmann, M. R., Chiu, W. L., Gomex-Gomex, L., Boller, T., Ausube, F. M. and Sheen, J. MAP kinase signaling cascade in *Arabidopsis* innate immunity. 2002 Nature 415:977-983. C
6. Ayliffe, M. A., Frost, D. V., Finnegan, E. J., Lawrence, G. J., Anderson, P. A. and Ellis, J. G. Analysis of alternative transcripts of the flax L6 rust resistance gene. 1999 Plant J. 17:287-292.
7. Berberich, T., Sano, H. and Kusano, T. Involvement of a MAP kinase, ZmMAPK5, in senescence and recovery from low-temperature stress in maize. 1999 Mol. Gen. Genet. 262:534-542.
8. Bogre, L., Ligterink, W., Meskiene, I., Barker, P. J., Heberle-Bors, E., Huskinsson, N. S., and Hirt, H. Wounding induces the rapid and transient activation of a specific MAK kinase pathway. 1997 Plant Cell 9:75-83.
9. Bohnert, H. J. Nelson, D. E. and Jensen, R. G. Adaption to environment stresses. 1995 Plant Cell 7:1099-1111.
10. Burnett, E. C., Desikan, R., Moser, R. C. and Neill, S. J. ABA activation of an MBP kinase in *Pisum sativum* epidermal peels correlates with stomatal responses to ABA. 2000 J. Exp. Bot. 51:197-205.
11. Cannman, C. E. and Kastan, M. B. Signal transduction. Three paths to stress relief 1996 Nature 384:213-214.
12. Cottyn, B., Outryve, M. F. van, Cleene, M. de, Swings, J. and Mew, T. W. Bacterial disease of rice. II Characterization of pathogenic bacteria associated with sheath rot complex and grain discoloration of rice in the Philippines. 1996 Plant Dis. 80:438-445.
13. Dinesh-Kumar, S. P. and Baker, B. J. alternatively spliced N resistance gene transcripts: their possible role in tobacco mosaic virus resistance. Proc. Natl. Acad. Sci. USA 97:1908-1913.
14. Frye, C. A., Tang, D. and Innes, R. W. Negative regulation of defense responses in plants by a conserved MAPKK kinase. Proc. Natl. Acad. Sci. USA. 98:373-378.
15. Gupta, R., Huang, Y., Kieber, J. and Luan, S. Identification of a dual-specificity protein phosphatase that inactivates a MAP kinase from *Arabidopsis*. 1998 Plant J. 16:581-589.
16. Hackett, R. M., Oh, S. A., Morris, P. C. and Grierson, D. A tomato MAP kinase kinase gene differentially regulated during fruit development, leaf senescence and wounding. 1998 Plant Physiol. 117:1526-1531.
17. Hardin, S. C. and Wolniak, S. M. Molecular cloning and characterization of maize ZmMEk1, a protein kinase with a catalytic domain homologous to mitogen- and stress-activated kinase kinases. 1998 Planta 206:577-584.
18. Harp, T. L ad Correll, J. C. Recovery and characterization of spontaneous, selenate-resistant mutants of *Magnaphthe grisea*, the rice blast pathogen. 1998 Mycologia 90:954-963.
19. He, C., Fong, S. H. Yang, D. and Wang, G. L. BWMK1, a novel MAP kinase induced by fungal infection and mechanical wounding in rice. 1999 Mol. Plant. Microbe Interact. 12:1064-1073.
20. Heimovaara-Dihkstra, S., Testerink, C. and Wang, M. Mitogen-actiated protein kinase and abscisic acid signal transduction. 2000 Result Probl Cell Differ. 27:131-144.
21. Hiei, Y., Ohta, S., Komari, T. and Kumashiro, T. Efficient transformation of rice (*Oryza saliva* L.) mediated by *Agrobacterium* and sequence analysis of the boundaries of the T-DNA 1994 Plant J. 6:271-282.
22. Hirt, H. Multiple roles of MAP kinases in plant signal transduction. 1997 Trends Plant Sci. 2:11-15.
23. Hofgen, R. and Willmitzer, L Storage of competent cells for *Agrobacterium* transformation. 1988 Nucleic Acids Res. 16:9877.
24. Huang, H. J., Fu., S. F., Tai, Y. H.; Chou, W. C. and Huang, D. D. Expression of *Oryza sativa* MAP kinase gene is developmentally regulated and stress-responsive. 2002 Physiologia Plantarum 114:572-580.
25. Huang, Y., Li H., Gupta, R., Morris, P. C., Luan, S and Kieber, J. J. ATMPK4, an *Arabidopsis* homology of mitogen-activated protein kinase, is activated in vitro by AtMEK1 through threonine phosphorylation. 2000 Plant Physiol. 122:1301-1310.
26. Ichimura, K., Mizoguchi, T., Hayashid, N., Seki, M, M. and Shinozaki, K. Molecular cloning and characterization of three cDNAs encoding putative mitogen-activated protein kinase kinases (MAPKKs) in *Arabidopsis* thatliana. 1998a DNA Res. 5:341-348.
27. Ichimura, K., Mizoguchi T., Irie, K., Morris, P. Giraudat, J., Matsumoto, K. and Shinozaki, K. Isolation of ATMEKK1 (a MAP kinase kinase)-interacting proteins and analysis of a MAP kinase cascade in *Arabidopsis*. 1998b Biochem. Biophy. Res. Commun. 253:532-543.
28. Ichimura, K., Shinozaki, K., Tena, G. Sheen, J. et al. Mitogen-activated protein kinase cascades in plants: a new nomenclature. 2002 Trends Plant Sci. 7:301-308.
29. Jia, Y. and Valent, B. Rapid determination of *Magnoporthe grisea* pathogenicity towards rice. 2001 Phytopathology 91:S44 (Abstract).
30. Jun, H. Axtell, M. J., Dahlbeck, D., Ekwenna, O., Zhang, S., Staskawicz, B. and Baker, B. NPK1, an MEKK1-like mitogen-activated protein kinase kinase kinase, regulates innate immunity and development in plants. 2002 Dev. Cell 3:291-297.
31. Jonak, C., Kiegerl, S., Ligterink, W., Baker, P. J., Juskisson, N.S, and Hirt, H. Stress signaling in plants: A mitogen-activated protein kinase pathway is activated by cold and drought. 1996 Proc. Natl. Acad. Sci. USA 93:11274-11279.
32. Khokhlatchev, A. V., Canagarajah, B., Wilsbacher, J., Robinson, M., Atkinson, M., Goldsmith, E. and Cobb, M. H. Phosphorylation of the MAP kinase ERK2 promotes its homodimerization and nuclear translocation. 1998 Cell 93:605-615.
33. Kieber, J. J., Rothenberg, M., Roman, G., Feldmann, K. A. and Ecker, J. R. CTR1, a negative regulator of the ethylene response pathway in *Arabidopsis*, encodes a member of the raf family of protein kinases. 1993 Cell 72:427-441.
34. Kiegerl, S., Cardinale, F., silligan, C., Gross, A., Baudouin, E., Liwosz, A., Eklof, S., Till, S., Bogre, L., Hirt, H. and Meskiene, I. SIMKK, a mitogen-activated protein kinase (MAPK) kinase, is a specific activator of the salt stress-induced MAPK, SIMK. 2000 Plant Cell 12:2247-2258.
35. RKnetsch, M. L., Wang, M., Snaar-Jagalska, B. E. and Heimovaara-Dijkstra, S. Abscisic acid induces mitogen-activated protein kinase activating in barley aleurone protoplasts. 1996 Plant Cell 8:11061-1067.
36. Kovtun, Y., Chiu, w.L., Tena, G. and Sheen, J. Functional analysis of oxidative stress-activated mitogen-activated protein kinase cascade in plants. 2000 Proc. Natl. Acad. Sci. USA 97:2940-2945.
37. Kutlz, D. Phylogenetic and functional classification of mitogen- and stress-activated protein kinases. 1998 J. Mol. Evol. 46:571-588.
38. Kyriakis, J. M. and Avruch, J. Protein kinase cascades activated by stress an inflammatory cytokines. 1996 Bioassays 18:567-577.
39. Lee, M-W., Qi, M. and Yang, Y. A novel jasmonic acid-inducible rice myb gene associate with fungal infection and host cell death. 2001 Mol. Plant. Microbe Interact. 14:527-535.
40. Leugang, J. and Giraudat, J. Abscisic acid signal transduction. 1998 Ann. Rev. Plant Physiol. Plant Mol. Biol. 49:199-222.
41. Ligterink, W. and Hirt, H. MAP kinase pathways in plants: Versatile signaling tools. 2000 Int. Rev. Cytol. 201:209-258.
42. Ligterink, W., Kroj, T., zur Nieden, U., Hirt, H., and Scheel, D. Receptor-mediated activation of a MAP kinase in pathogen defense of plants. 1997 Science 276, 20542057.
43. Lopez, A. J. Alternative splicing of pre-mRNA: developmental consequences and mechanisms of regulation. 1998 Annu. Rev. Genet. 32, 279-305.
44. Marchetti, M. A., Rush, M. C., and Hunter, W. E. Current status of rice blast [*Pyriculaia oryzae*] in the southern United States. Plant Dis. Rep. 60, 721-725.
45. Meskiene, I., Bogre, L., Glaser, W., Balog, J., Brandstotter, M., Zwerger, K., Ammerer, G., and Hirt, H. MP2C, a plant protein phosphatase 2C, functions as a negative regulator of mitogen-activated protein kinase pathways in yeast and plants. 1998 Proc. Natl. Acad. Sci. USA 95, 1938-1943.
46. Midoh, N., and Iwate, M. Cloning and characterization of probenazole-inducible gene for an intracellular pathogenesis-related protein in rice. 1996 Plant Cell Physiol. 37, 9-18.
47. Mikolajczyk, M., Awotunde, O, S., Muszynska, G., Klessig, D. F., and Dobrowolska, G. Osmotic stress induces rapid activation of a salicylic acid-induced protein kinase and a homolog of protein kinase ASK1 in tobacco cells. 2000 Plant Cell 12, 165-178.
48. Mittler, R., and Rizhsky, L. Transgene-induced lesion mimic. 2000 Plant Mol. Biol. 44, 335-344.
49. Mizoguchi, T., Hayashida, N., Yamaguchi-Shinozachi, K., Kamada, H., and Shinozachi, K. ATMPKs: a gene family of plant MAP kinases in *Arabidopsis thaliana*. 1993 FEBS Lett. 336, 440-444.
50. Mizoguchi, T., Ichimura, K., and Shinozaki, K. (1997). Environmental stress response in plants: The role of mitogen-activated protein kinases. 1997 Trends Biotechnol. 15, 15-19
51. Molina, A., Volrath, S., Guyer, D., Maleck, K., Ryals, J., and Ward, E. (1999). Inhibition of protoporphyrinogen oxidase expression in *Arabidopsis* causes a lesion-mimic phenotype that induces systemic acquired resistance. 1999 Plant J. 17, 667-678.
52. Morris, P. C., Guerrier, D., Leung, J., and Giraudat, J. (1997). Cloning and characterisation of MEK1, an *Arabidopsis* gene encoding a homologue of MAP kinase kinase. 1997 Plant Mol. Biol. 35, 1057-1064.
53. Munnik, T., Ligterink, W., Meskiene, I., Calderini, O., Beyerly, J., Musgrave, A., and Hirt, H. (1999). Distinct osmo-sensing protein kinase pathways are involved in signalling moderate and severe hyper-osmotic stress. 1999 Plant J. 20, 381-388.
54. Nishihama, R., Banno, H., Kawahara, E., Irie, K., and Machida, Y. (1997). Possible involvement of differential splicing in regulation of the activity of *Arabidopsis* ANP1 that is related to mitogen-activated protein kinase kinase kinases (MAPKKKs). 1997 Plant J. 12, 39-48.
55. Parker, J. E., Coleman, M. J., Szabo, V., Frost, L. N., Schmidt, R., van der Biezen, E. A., Moores, T., Dean, C., Daniels, M. J., and Jones, J. D. The *Arabidopsis* downy mildew resistance gene RPP5 shares similarity to the toll and interleukin-1 receptors with N and L6. 1997 Plant Cell 9, 879-894.
56. Petersen, M., Brodersen, P., Naested, H., Andreasson, E., Lindhart, U., Johansen, B., Nielsen, H. B., Lacy, M., Austin, M. J., Parker, J. E., Sharma, S. B., Klessig, D. F., Martienssen, R., Mattsson, O., Jensen, A. B., and Mundy, J. *Arabidopsis* map kinase 4 negatively regulates systemic acquired resistance. 2000 Cell 103, 1111-1120.

57. Qi, M., and Yang, Y. Quantification of *Magnaporthe grisea* during infection of rice plants using real-time PCR and northern blot/phosphoimaging analysis. 2002 Phytopathology 92: (in press).
58. Reymond, P., and Farmer, E. E. Jasmonate and salicylate as global signals for defense gene expression. 1998 Curr. Opin. Plant Biol. 1, 404-411.
59. Saijo, Y., Hata, S., Kyozuka, J., Shimamoto, K., and Izui, K. Over-expression of a single Ca2+-dependent protein kinase confers both cold and salt/drought tolerance on rice plants. 2000 Plant J. 23, 319-327.
60. Sambrook, J., Fritsch, E. F., and Maniatis, T. 1989 Molecular Cloning: A Laboratory Manual, 2nd ed. (Cold Spring Harbor, N. Y.: Cold Spring Harbor Laboratory Press).
61. Seger, R., and Krebs, E. G. The MAPK signaling cascade. 1995 FASEB J. 9, 726-735.
62. Seo, S., Okamoto, M., Seto, H., Ishizuka, K., Sano, H., and Ohashi, Y. Tobacco MAP kinase: A possible mediator in wound signal transduction pathways. 1995 Science 270, 1988-1992.
63. Seo, S., Sano, H., and Ohashi, Y. Jasmonate-based wound signal transduction requires activation of WIPK, a tobacco mitogen-activated protein kinase. 1999 Plant Cell 11, 289-298.
64. Samuel, M. A., and Ellis, B. E. Double jeopardy: both overexpression and suppression of a redox-activated plant mitogen-activated protein kinase render tobacco plants ozone sensitive. 2002 Plant Cell 14, 2059-2069.
65. Snedden, W. A., and Blumwald, E. Alternative splicing of a novel diacylglycerol kinase in tomato leads to a calmodulin-binding isoform. 2000 Plant J. 24, 317-326.
66. Song, F., and Goodman, R. M. OsBIMK1, a rice MAP kinase gene involved in disease resistance response. 2002 Planta 215, 997-1005.
67. Stone, J. M., and Walker, J. C. Plant protein kinase families and signal transduction. 1995 Plant Physiol. 108, 451-457
68. Suzuki, K., and Shinshi, H. Transient activation and tyrosine phosphorylation of a protein kinase in tobacco cells treated with a fungal elicitor. 1995 Plant Cell 7, 639-647.
69. Takezawa, D. Elicitor- and A23187-induced expression of WCK-1, a gene encoding mitogen-activated protein kinase in wheat. 1999 Plant Mol. Biol. 40, 921-933.
70. Tang, X., Frederick, R. D., Zhou, J., Halternan, D. A., Jia, Y., and Martin, G. B. Initiation of plant disease resistance by physical interaction of AvrPto and Pto kinase. 1996 Science 274, 2060-2063.
71. Tena, G., Asai, T., Chiu, W. L., and Sheen, J. Plant mitogen-activated protein kinase signaling cascades. 2001 Curr. Opin. Plant Biol. 4, 392-400.
72. Usami, S., Banno, H., Ito, Y., Nishihama, R., and Machida, Y. Cutting activates a 46-kilodalton protein kinase in plants. 1995 Proc. Natl. Acad. Sci. USA 92, 8660-8664.
73. Wen J.-Q., Oono, K., and Imai, R. Two novel mitogen-activated protein signaling components, OsMEK1 and OsMAP1, are involved in a moderate low-temperature signaling pathway in rice. 2002 Plant Physiol. 129, 1880-1891.
74. Winans, S. C., Kerstetter, R. A. and Nester, E. W. Transcriptional regulation of the virA and virg genes of *Agrobacterium tumefaciens*. 1998 J. Bacteriol. 170, 4047-4054.
75. Xiong, L., Lee, M. W., Qi, M., and Yang Y. Identification of defense-related rice genes by suppression subtractive hybridization and differential screening. 2001 Mol. Plant. Microbe Interact. 14, 685-692.
76. Yang, K. Y., Liu, Y., and Zhang, S. Activation of a mitogen-activated protein kinase pathway is involved in disease resistance in tobacco. 2001 Proc. Natl. Acad. Sci. USA 98, 741-746.
77. Yang, Y., Shah, J., and Klessig, D. F. Signal perception and transduction in plant defense responses. 1997 Genes Dev. 11, 1621-1639.
78. Zhang, F., Strand, A-, Robbins, D., Cobb, M. H., and Goldsmith, E. J. Atomic structure of the MAP kinase ERK2 at 2.3 Å resolution. 1994 Nature 367, 704-711.
79. Zhang, Q., Saghai Maroof, M. A., Lu, T. Y., and Shen, B. Z. Genetic diversity and differentiation of indica and japonica rice detected by RFLP analysis. 1992 Theor. Appl. Genet. 83, 495-499.
80. Zhang, S., and Klessig, D. F. Salicylic acid activates a 48-kD MAP kinase in tobacco. 1997 Plant Cell 9, 809-824.
81. Zhang, S., and Klessig, D. F. The tobacco wounding-activated mitogen-activated protein kinase is encoded by SIPK. 1998a Proc. Natl. Acad. Sci. USA 95, 7225-7230.
82. Zhang, S., and Klessig, D. F. Resistance gene N-mediated de novo synthesis and activation of a tobacco mitogen-activated protein kinase by tobacco mosaic virus infection. 1988b Proc. Natl. Acad. Sci. USA 95, 7433-7438.
83. Zhang, S., and Kiessig, D. F. MAPK cascades in plant defense signaling. 2001 Trends Plant Sci. 6, 520-527.
84. Zhang, S., and Liu, Y. Activation of salicylic acid-induced protein kinase, a mitogen-activated protein kinase, induces multiple defense responses in tobacco. 2001 Plant Cell 13, 1877-1889.

---

What is claimed is:

1. A transgenic plant cell comprising an isolated nucleic acid molecule which comprises a nucleotide sequence selected from the group consisting of: a) a nucleotide sequence as set forth in SEQ ID NO:1; and b) a nucleotide sequence encoding a polypeptide having an amino acid sequence as set forth in SEQ ID NO:2; wherein expression of said nucleotide sequence increases tolerance to low temperature of 4° C., salinity and drought in the plant cell compared to an untransformed plant cell of the same species.

2. A transgenic plant comprising an isolated nucleic acid molecule which comprises a nucleotide sequence selected from the group consisting of: a) a nucleotide sequence as set forth in SEQ ID NO:1; and b) a nucleotide sequence encoding a polypeptide having an amino acid sequence as set forth in SEQ ID NO:2; wherein expression of said nucleotide sequence increases tolerance to low temperature of 4° C., salinity and drought in the plant compared to an untransformed plant of the same species.

3. A transgenic seed obtained from the transgenic plant of claim 2, wherein the seed comprises the nucleic acid molecule.

4. A method of producing a transgenic plant with increased tolerance to abiotic stress, said method comprising transforming a plant cell with an isolated nucleic acid molecule which comprises a nucleotide sequence encoding the polypeptide as set forth in SEQ ID NO: 2, and growing said plant cell into the transgenic plant, wherein said plant expressing the nucleotide sequence has increased tolerance to said abiotic stress, and wherein said abiotic stress is low temperature of 4° C., salinity, and drought.

* * * * *